(12) United States Patent
Hoffman

(10) Patent No.: US 11,505,355 B2
(45) Date of Patent: Nov. 22, 2022

(54) PHARMACY ORDER PROCESSING SYSTEM WORKSTATIONS AND RELATED METHODS

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 262 days.

(21) Appl. No.: 17/102,774

(22) Filed: Nov. 24, 2020

(65) Prior Publication Data

US 2021/0078747 A1 Mar. 18, 2021

Related U.S. Application Data

(63) Continuation of application No. 16/226,944, filed on Dec. 20, 2018, now Pat. No. 10,865,006, which is a
(Continued)

(51) Int. Cl.
| | |
|---|---|
| *B65B 69/00* | (2006.01) |
| *B25J 9/00* | (2006.01) |
| *B25J 9/16* | (2006.01) |
| *G16H 20/13* | (2018.01) |
| *A61J 1/00* | (2006.01) |
| *G16H 20/17* | (2018.01) |

(52) U.S. Cl.
CPC ............ *B65B 69/0033* (2013.01); *A61J 1/00* (2013.01); *B25J 9/0096* (2013.01); *B25J 9/1679* (2013.01); *G16H 20/13* (2018.01); *G16H 20/17* (2018.01)

(58) Field of Classification Search
CPC ....... B65B 69/0033; A61J 1/00; B25J 9/0096; B25J 9/1679; B25J 21/005; G16H 20/13; G16H 20/17; G16H 40/20
See application file for complete search history.

(56) References Cited

U.S. PATENT DOCUMENTS 3,939,998 A * 2/1976 Soltermann ............... G21F 9/00
414/412
4,944,647 A 7/1990 Oleson
(Continued)

*Primary Examiner* — Thomas Randazzo

(57) ABSTRACT

A container disassembly workstation for a pharmacy order processing system includes a base, a desktop connected to the base and defining a container disassembly workspace, and a pharmaceutical receptacle assembly extending through the desktop. The pharmaceutical receptacle assembly includes a pharmaceutical dust separation screen configured to retain pharmaceuticals and to permit pharmaceutical dust to pass through the pharmaceutical dust separation screen. The pharmaceutical receptacle assembly also includes a pharmaceutical dust receptacle configured to receive the pharmaceutical dust separation screen and pharmaceutical dust from the pharmaceuticals. The pharmaceutical receptacle assembly further includes a pharmaceutical receptacle positioned adjacent to the pharmaceutical dust receptacle, wherein the pharmaceutical receptacle includes a pharmaceutical receptacle funnel configured to receive the pharmaceuticals from the pharmaceutical dust separation screen and a door hingeably connected to the pharmaceutical receptacle funnel and configured to move between an open position and a closed position.

22 Claims, 22 Drawing Sheets

Related U.S. Application Data continuation-in-part of application No. 15/996,909, filed on Jun. 4, 2018, now Pat. No. 10,695,902.

(56) References Cited

U.S. PATENT DOCUMENTS

| | | | |
|---|---|---|---|
| 5,720,154 A | 2/1998 | Lasher | |
| 5,771,657 A | 6/1998 | Lasher | |
| 6,026,561 A | 2/2000 | Lafond | |
| 6,769,228 B1 | 8/2004 | Mahar | |
| 6,892,512 B2 | 5/2005 | Rice | |
| 7,185,477 B2 | 3/2007 | Rice | |
| 7,530,211 B2 | 5/2009 | McErlean | |
| 7,765,776 B1 | 8/2010 | Leu | |
| 8,117,809 B2 | 2/2012 | McErlean | |
| 8,539,742 B2 | 9/2013 | McErlean | |
| 8,600,903 B2 | 12/2013 | Eller | |
| 9,242,751 B1 | 1/2016 | Joplin | |
| 9,567,119 B2 | 2/2017 | Joplin | |
| 9,639,668 B2 | 5/2017 | Joplin | |
| 2004/0090153 A1 | 5/2004 | Touzani | |
| 2004/0123567 A1* | 7/2004 | McErlean | B65C 9/0015 53/445 |
| 2005/0279745 A1 | 12/2005 | Gupta | |
| 2006/0162298 A1 | 7/2006 | Oh | |
| 2009/0211198 A1* | 8/2009 | McErlean | G16H 20/13 414/412 |
| 2010/0258565 A1 | 10/2010 | Isaacson | |
| 2012/0109081 A1 | 5/2012 | Romano | |
| 2013/0000260 A1* | 1/2013 | McErlean | G16H 70/40 53/492 |
| 2013/0019993 A1* | 1/2013 | Roura Adell | B65B 69/0058 141/98 |
| 2018/0144285 A1 | 5/2018 | Hoffman | |
| 2019/0126331 A1 | 5/2019 | Vanderwoude | |

* cited by examiner

PHARMACY ORDER PROCESSING SYSTEM WORKSTATIONS AND RELATED METHODS

CROSS-REFERENCE TO RELATED APPLICATIONS

This application claims priority to and is a continuation application of U.S. patent application Ser. No. 16/226,944, filed on Dec. 20, 2018; said application Ser. No. 16/226,944 being a continuation-in-part of U.S. patent application Ser. No. 15/996,909, filed Jun. 4, 2018 and now issued as U.S. Pat. No. 10,695,902; the entire disclosures of which are hereby incorporated by reference in their entirety.

FIELD

The present disclosure relates generally to the technical field of pharmacy order processing, and more particularly, to methods and systems for removing pharmaceuticals from relatively small volume pharmaceutical containers and transferring the removed pharmaceuticals to relatively larger volume pharmaceutical containers using container disassembly workstations, especially in a high volume, specialty, or partially-automated order processing center.

BACKGROUND

Pharmaceutical order processing systems typically involve labor intensive processes to remove pharmaceuticals from manufacturer packaging, transfer the pharmaceuticals to a bulk storage container, retrieve the pharmaceuticals, and fill and package the many pharmacy orders. Many of the pharmacy orders are custom orders that require a quantity of specific pharmaceuticals that necessitates emptying multiple original manufacturer containers to fill a single order, and thus the process for filling the orders is difficult to efficiently complete and requires substantial operator interaction throughout the process.

This background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

A container disassembly workstation for a pharmacy order processing system includes a base, a desktop connected to the base and defining a container disassembly workspace, and a pharmaceutical receptacle assembly extending through the desktop. The pharmaceutical receptacle assembly includes a pharmaceutical dust separation screen configured to retain pharmaceuticals and to permit pharmaceutical dust to pass through the pharmaceutical dust separation screen. The pharmaceutical receptacle assembly also includes a pharmaceutical dust receptacle configured to receive the pharmaceutical dust separation screen and pharmaceutical dust from the pharmaceuticals. The pharmaceutical receptacle assembly further includes a pharmaceutical receptacle positioned adjacent to the pharmaceutical dust receptacle, wherein the pharmaceutical receptacle includes a pharmaceutical receptacle funnel configured to receive the pharmaceuticals from the pharmaceutical dust separation screen and a door hingeably connected to the pharmaceutical receptacle funnel and configured to move between an open position and a closed position.

A pharmacy order processing system includes a container disassembly workstation for a pharmacy order processing system. The container disassembly workstation includes a base, a desktop connected to the base and defining a container disassembly workspace, and a pharmaceutical receptacle assembly extending through the desktop. The pharmaceutical receptacle assembly includes a pharmaceutical dust separation screen configured to retain pharmaceuticals and to permit pharmaceutical dust to pass through the pharmaceutical dust separation screen. The pharmaceutical receptacle assembly also includes a pharmaceutical dust receptacle configured to receive the pharmaceutical dust separation screen and pharmaceutical dust from the pharmaceuticals. The pharmaceutical receptacle assembly further includes a pharmaceutical receptacle positioned adjacent to the pharmaceutical dust receptacle, wherein the pharmaceutical receptacle includes a pharmaceutical receptacle funnel configured to receive the pharmaceuticals from the pharmaceutical dust separation screen and a door hingeably connected to the pharmaceutical receptacle funnel and configured to move between an open position and a closed position. The container disassembly workstation includes a bulk container area including a plurality of bulk containers, a bulk container of the plurality of bulk containers configured to receive the pharmaceuticals from the pharmaceutical receptacle.

A method of disassembling a container includes opening, within a container disassembly workspace of a container disassembly workstation, a container containing pharmaceutical products including pharmaceuticals and packing materials. The method also includes transferring the pharmaceutical products from the opened container to a pharmaceutical dust separation screen of a pharmaceutical receptacle assembly, wherein the pharmaceutical dust separation screen is configured to retain the pharmaceuticals and to permit pharmaceutical dust to pass through the pharmaceutical dust separation screen. The method further includes separating the pharmaceuticals from the pharmaceutical dust and the packing materials and moving the pharmaceuticals from a pharmaceutical dust receptacle of the pharmaceutical receptacle assembly to a pharmaceutical receptacle. The pharmaceutical receptacle includes a pharmaceutical receptacle funnel configured to receive the pharmaceuticals from the pharmaceutical dust separation screen and a door hingeably connected to the pharmaceutical receptacle funnel and configured to move between an open position and a closed position. The method also includes disposing of the packing materials.

A method of disassembling a container includes moving a container containing pharmaceutical products including pharmaceuticals and packing materials from a first position at a container staging area to a second position at a cutter device. The method also includes cutting, with the cutter device, the container into a first portion and a second portion, wherein the pharmaceutical products are retained in the second portion. The method further includes transferring the pharmaceutical products from the second portion to a pharmaceutical dust separation screen of a pharmaceutical receptacle assembly. The pharmaceutical dust separation screen is configured to retain the pharmaceuticals and to permit pharmaceutical dust to pass through the pharmaceutical dust separation screen. The method also includes separating the pharmaceuticals from the pharmaceutical dust and the packing materials.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

In the drawings, reference numbers may be reused to identify similar and/or identical elements.

DETAILED DESCRIPTION

Example systems and methods for processing a pharmacy order, for example, in a pharmacy, are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a pharmacy, and in some embodiments a high volume pharmacy. The prescription order may include more than one pharmaceutical, or prescription drug, for fulfillment. Each pharmaceutical in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a pharmaceutical contained therein, the pharmaceuticals being required for the orders in varying and sometimes numerous quantities.

As described herein, pharmaceutical order processing systems typically involve labor intensive processes to remove pharmaceuticals from manufacturer packaging, transfer the pharmaceuticals to a bulk storage container, retrieve the pharmaceuticals, and fill and package the many pharmacy orders. The container disassembly workstation described herein presents an improved system and method for filling pharmacy orders at a high volume to improve order fulfillment realization and customer satisfaction. The container disassembly workstation includes a base, a desktop connected to the base, the desktop defining a container disassembly workspace, and a pharmaceutical receptacle assembly extending through the desktop. The pharmaceutical receptacle assembly includes a pharmaceutical dust separation screen configured to retain pharmaceuticals and to permit pharmaceutical dust to pass through the pharmaceutical dust separation screen. A pharmaceutical dust receptacle of the pharmaceutical receptacle assembly is configured to receive the pharmaceutical dust separation screen and pharmaceutical dust from the pharmaceuticals, and a pharmaceutical receptacle is positioned adjacent to the pharmaceutical dust receptacle. The pharmaceutical receptacle receives the pharmaceuticals from the pharmaceutical dust separation screen and a door hingeably connected to the pharmaceutical receptacle and configured to move between an open position and a closed position. A bulk container is positioned below the pharmaceutical receptacle in a bulk container area and receives the pharmaceuticals from the pharmaceutical receptacle.

Figure 1:
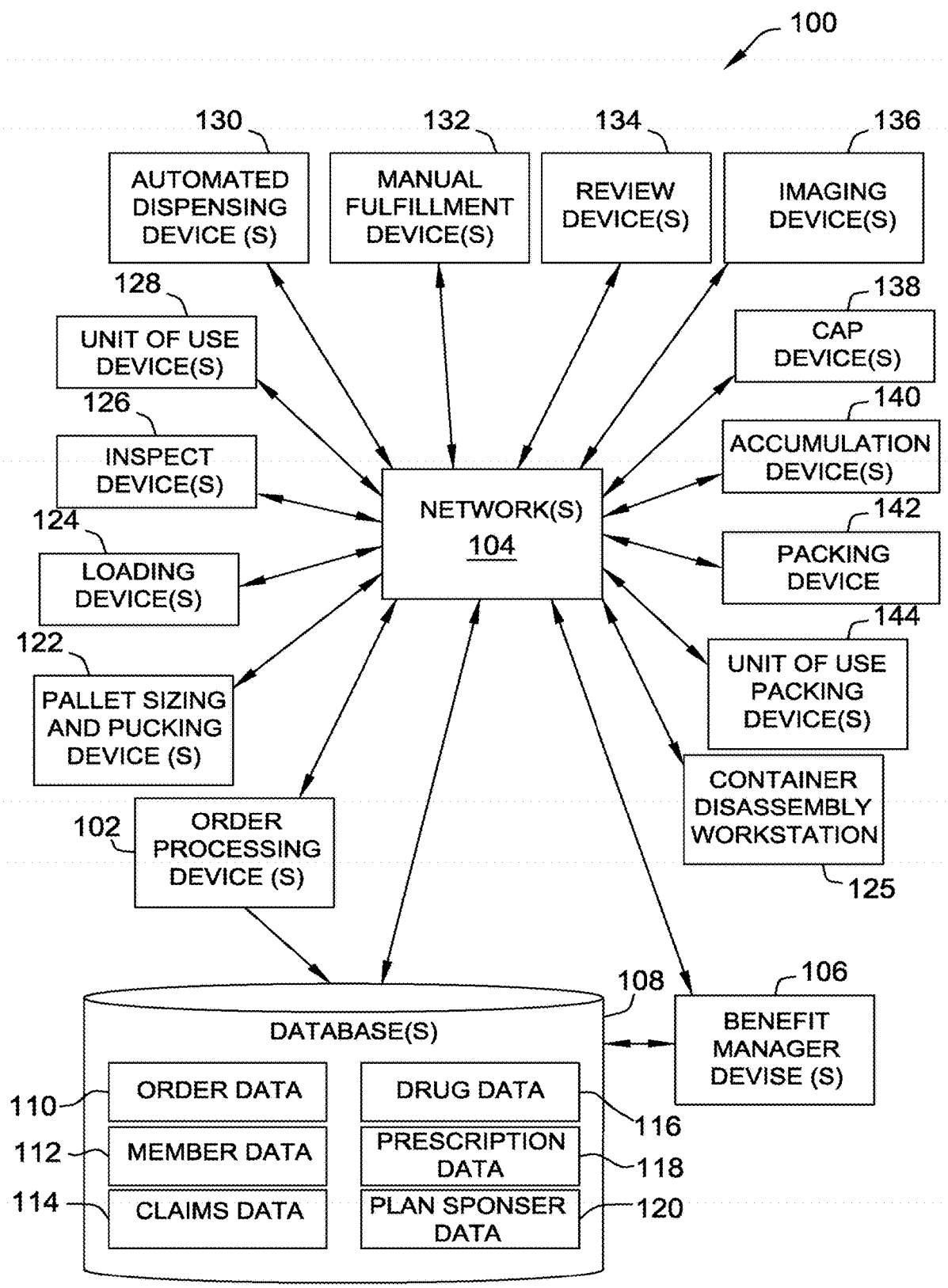
FIG. 1 is a block diagram of an example implementation of a pharmacy order processing system, according to an example embodiment.

FIG. 1 is a block diagram of an example system 100, according to an example embodiment. While the system 100 is generally described as being deployed in a high volume fulfillment center (e.g., a mail order pharmacy, a direct delivery pharmacy, and the like), the system 100 and/or components thereof may otherwise be deployed. The system 100 may include an order processing device 102 in communication with a benefit manager device 106 over a network 104. Additional devices which may be in communication with the benefit manager device 106 and/or the order processing device 102 over network 104 include: database(s) 108, pallet sizing and pucking device(s) 122, loading device(s) 124, inspect device(s) 126, unit of use device(s) 128, automated dispensing device(s) 130, manual fulfillment device(s) 132, review device(s) 134, imaging device(s) 136, cap device(s) 138, accumulation device(s) 140, packing device(s) 142, unit of use packing device(s) 144, and container disassembly workstation(s) 125 configured to disassembly small containers.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device physically separate from a pharmacy that enables communication with other devices located within a pharmacy. For example, the order processing device 102 may be in communication with another order processing device 102 and/or other devices 122-144 located within a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate in combination with the benefit manager device 106.

Examples of the order processing device 102 include a set-top box (STB), a receiver card, a mobile telephone, a personal digital assistant (PDA), a display device, a portable gaming unit, a tablet, and a computing system; however other devices may also be used. For example, the order processing device 102 may include a mobile electronic device, such an iPhone or iPad device by Apple, Inc., mobile electronic devices powered by ANDROID by Google, Inc., and a BLACKBERRY device by Blackberry Limited. The order processing device 102 may also include other computing devices, such as desktop computing devices, notebook computing devices, netbook computing devices, gaming devices, and the like. The device 102 may include a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While the benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage) and/or through the network 104 (e.g., in a cloud configuration or software as a service) with a database 108 (e.g., as may be retained in memory or otherwise). The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) a prescription container (e.g., a prescription bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the PBM. The information stored as member data 112 may include personal information, personal health information, protected health information, and the like. Examples of the member data 112 include name, address, telephone number, e-mail address, prescription drug history, etc., and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in the pharmacy benefit plan being provided by the PBM. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114. The claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form, etc.), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.). In some embodiments, the order data 110 may be linked to associated member data 112, claims data 114, drug data 116, and/or prescription data 118.

The plan sponsor data 120 includes information regarding the plan sponsors of the PBM. Examples of the plan sponsor data 120 include company name, company address, contact name, contact telephone number, contact e-mail address, and the like.

The order processing device 102 may direct at least some of the operations of devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more than one of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of the prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 102 based on prescriptions which the order processing device 102 decides to launch. In general, prescription orders in the storage device 108 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, pick and place mechanism, or the like. In one embodiment, the loading device 108 has robotic arms or pickers to grasp a prescription container and move it to and from a pallet or a puck. The loading device 124 may also print a label which is appropriate for a container that is to be loaded onto the pallet, and apply the label to the container. The pallet may be located on a conveyor assembly during these operations, e.g., at the high volume fulfillment center.

The inspect device 126 may verify that containers in a pallet are correctly labeled and in the correct spot on the pallet. The inspect device 126 may scan the label on one or more than one container on the pallet. Labels of the containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 128 may be packaged individually or collectively for shipping, or may be shipped in combination with other prescription drugs dispenses by other devices in the high volume fulfillment center.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high volume fulfillment center.

The manual fulfillment device 132 may provide for manual fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap, although this process may be performed by a subsequent device in the high volume fulfillment center.

The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise.

The packing device 142 packages a prescription order in preparation for shipping the order. The packing device 142 may box, bag, or otherwise package the fulfilled prescription order for delivery. The packing device 142 may further place inserts into the packaging. For example, bulk prescription orders may be shipped in a box, while other prescription orders may be shipped in a bag which may be a wrap seal bag. The packing device 142 may label the box or bag with the address and a recipient's name. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise.

The unit of use packing device 144 packages a unit of use prescription order in preparation for shipping the order. The unit of use packing device 144 may include manual scanning of containers to be bagged for shipping to verify each container in the order.

While the system 100 in FIG. 1 is shown to include single devices 102, 106, and 122-144, multiple devices may be used. The devices 102, 106, and 122-144 may be the same type or model of device or may be different device types or models. When multiple devices are present, the multiple devices may be of the same device type or models or may be a different device type or model. The types of devices 102, 106, and 122-144 shown in FIG. 1 are example devices. In other configurations of the system 100, lesser, additional, or different types of devices may be included.

Moreover, the system 100 shows a single network 104; however, multiple networks can be used. The multiple networks may communicate in series with each other to link the devices 102, 106, and 122-144 or in parallel to link the devices 102, 106, and 122-144. Multiple devices may share processing and/or memory resources. The devices 102, 106, and 122-144 may be located in the same area or in different locations. For example, the devices 102, 106, and 122-144 may be located in a building or set of adjoining buildings. The devices 102, 106, and 122-144 may be interconnected (e.g. by conveyors), networked, and/or otherwise in contact with one another or integrated with one another, e.g., at the high volume fulfillment center. In addition, the functionality of a device may be split among a number of discrete devices and/or combined with other devices.

Figure 2:
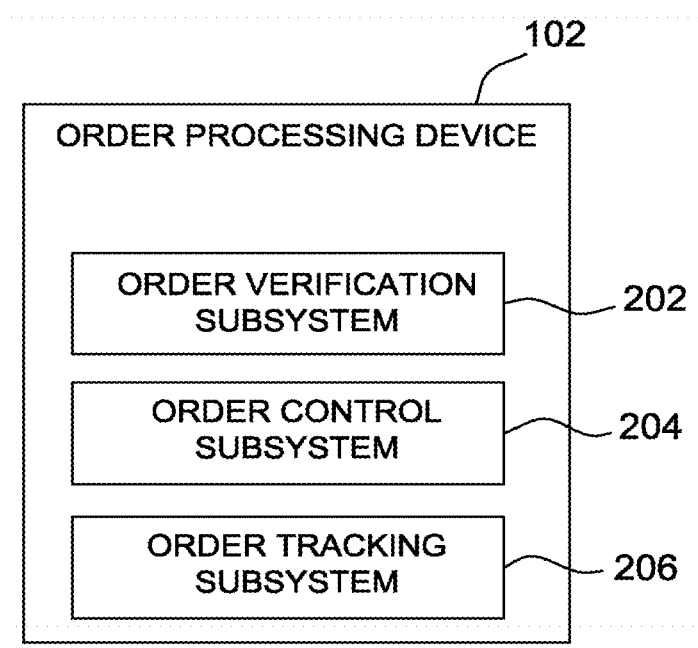
FIG. 2 is a block diagram of an example order processing device that may be deployed within the system of FIG. 1, according to an example embodiment.

FIG. 2 illustrates the order processing device 102, according to an example embodiment. The order processing device 102 may be used by one or more than one operator to generate prescription orders, make routing decisions, make prescription order consolidation decisions, and/or view order status and other order related inflammation. For example, the prescription order may be comprised of order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR Other communications between the order verification subsystem 202 and the benefit manager device 106 may be performed for a variety of purposes.

The order control subsystem 204 controls various movements of the containers and/or pallets along with various filling functions during their progression through the system 100. In some embodiments, the order control subsystem 204 may identify the prescribed drug in one or more than one prescription order as capable of being fulfilled by the automated dispensing device 130. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130. As the devices 122-144 may be interconnected by a system of conveyors or other container movement systems, the order control subsystem 204 may control various conveyors to deliver the pallet from the loading device 124 to the manual fulfillment device 132, for example.

The order tracking subsystem 206 may track a prescription order as it progresses (or stops) toward fulfillment. The order tracking subsystem 206 may track, record and/or update order history, order status or the like. The order tracking subsystem 206 may store data locally (e.g., in a memory) or as a portion of the order data 110 stored in the storage device 108.

Figure 3:
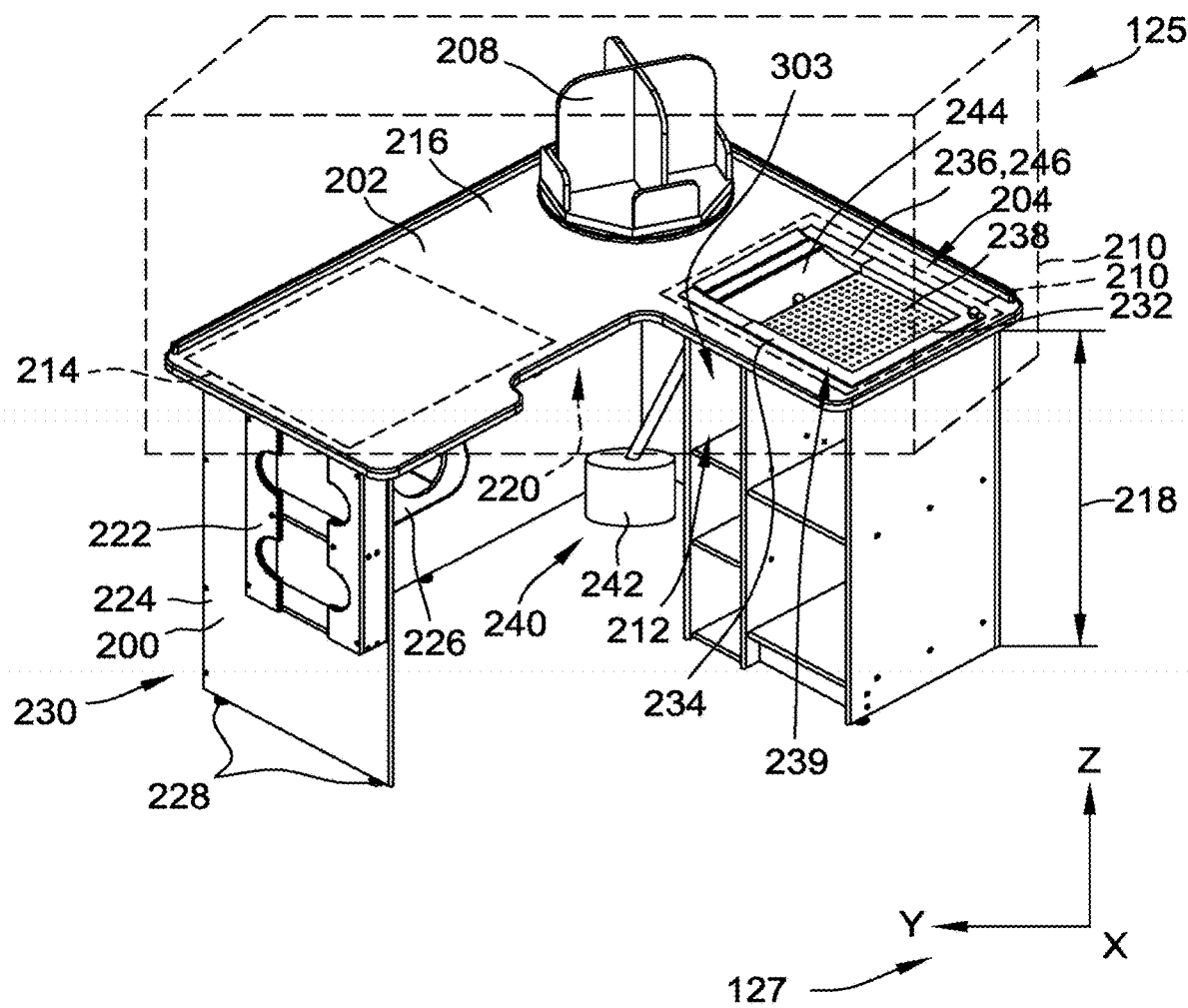
FIG. 3 is perspective view of a container disassembly workstation for use with the system shown in FIG. 1, according to an example embodiment.
Figure 4:
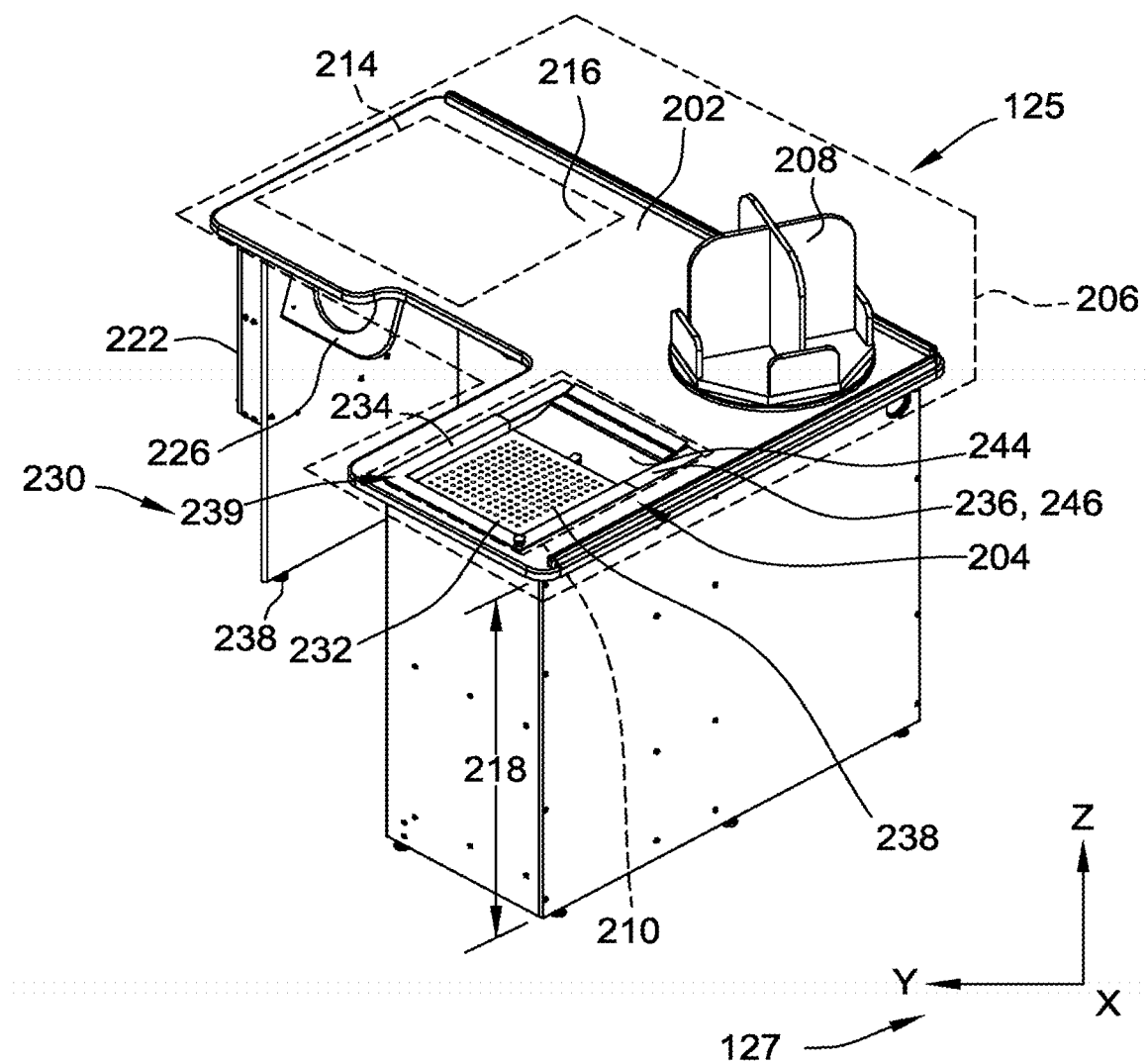
FIG. 4 is another perspective view of the container disassembly workstation shown in FIG. 3, according to an example embodiment.
Figure 5:
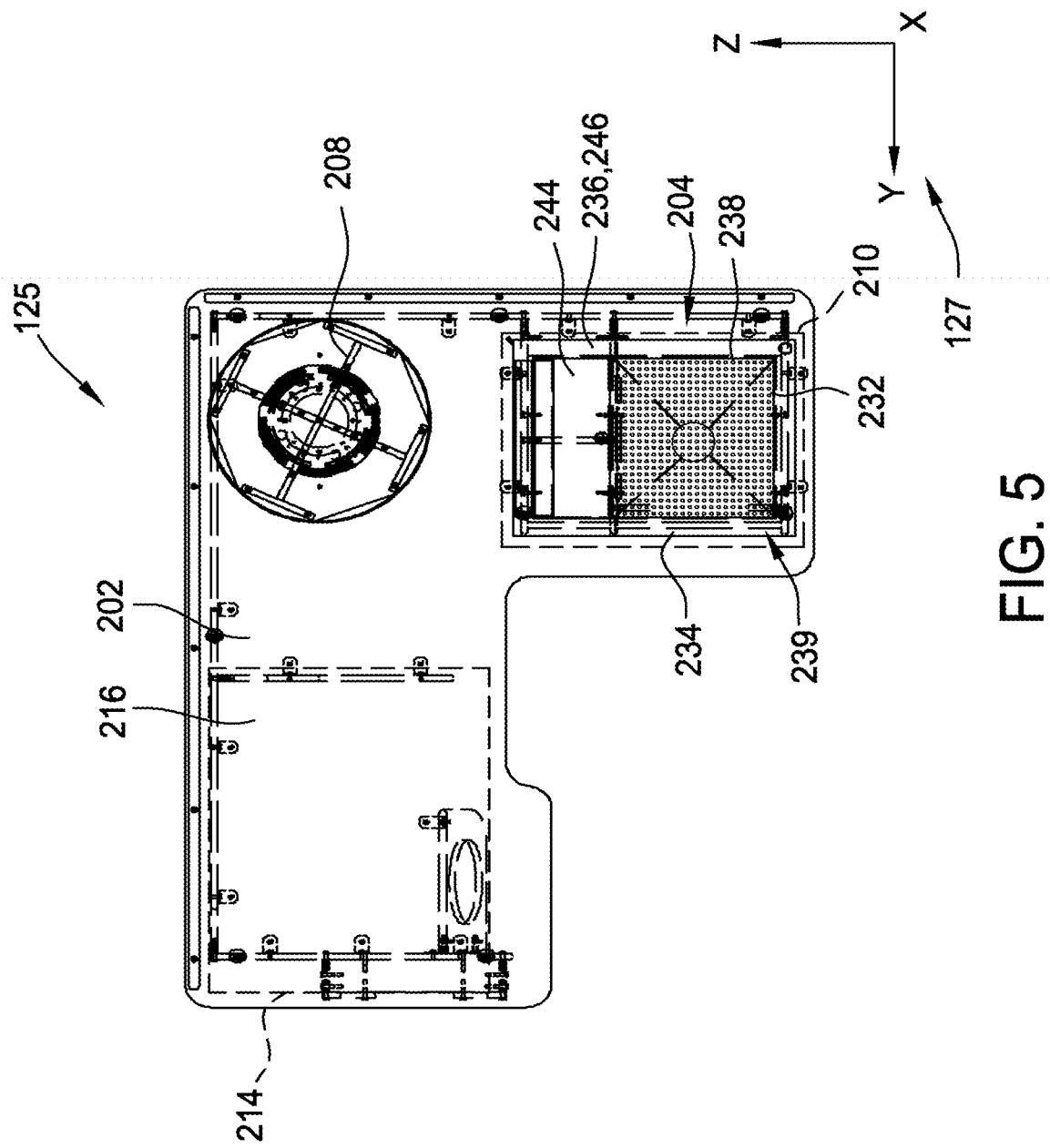
FIG. 5 is a top view of the container disassembly workstation shown in FIG. 3, according to an example embodiment.
Figure 6:
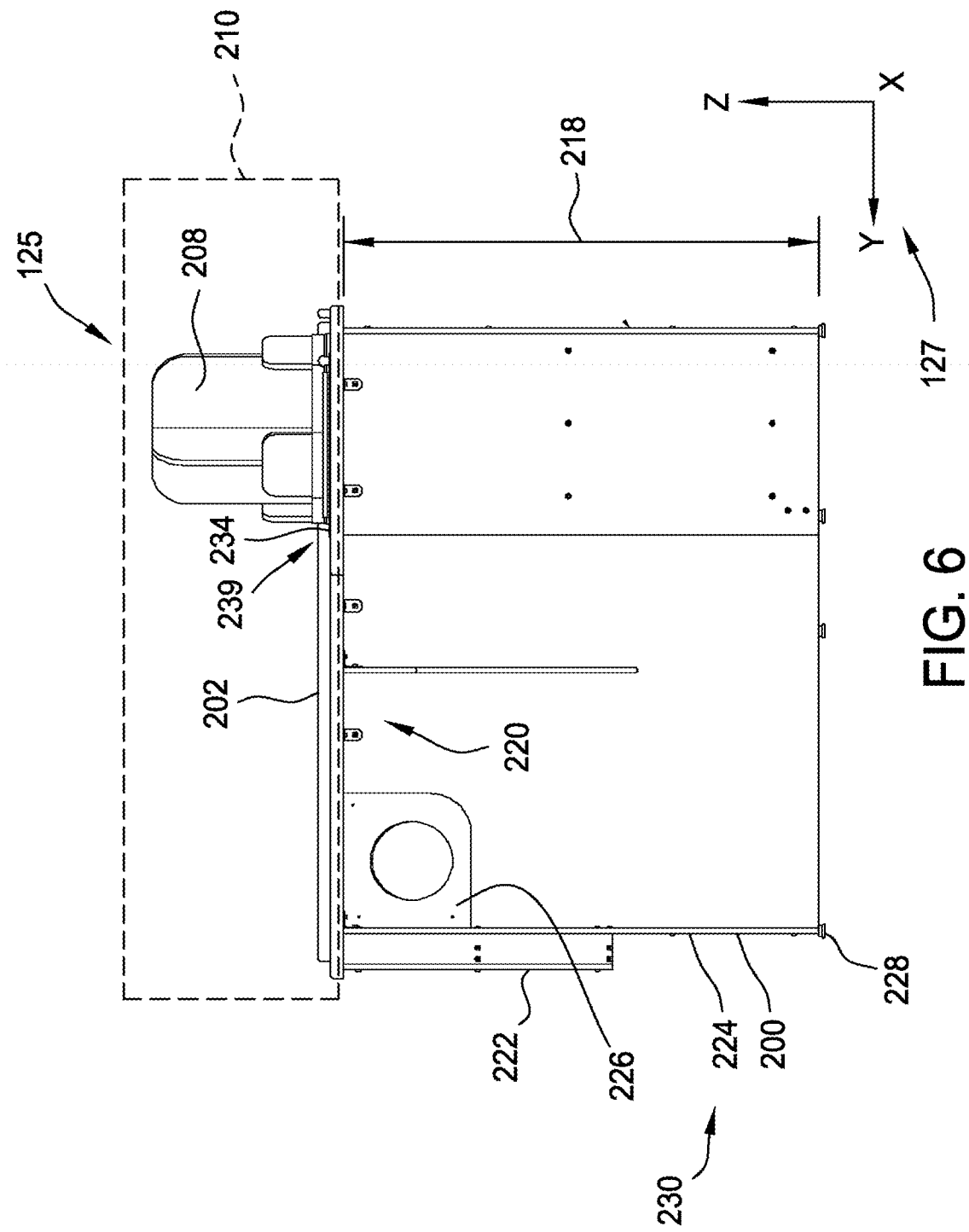
FIG. 6 is a front view of the container disassembly workstation shown in FIG. 3, according to an example embodiment.
Figure 7:
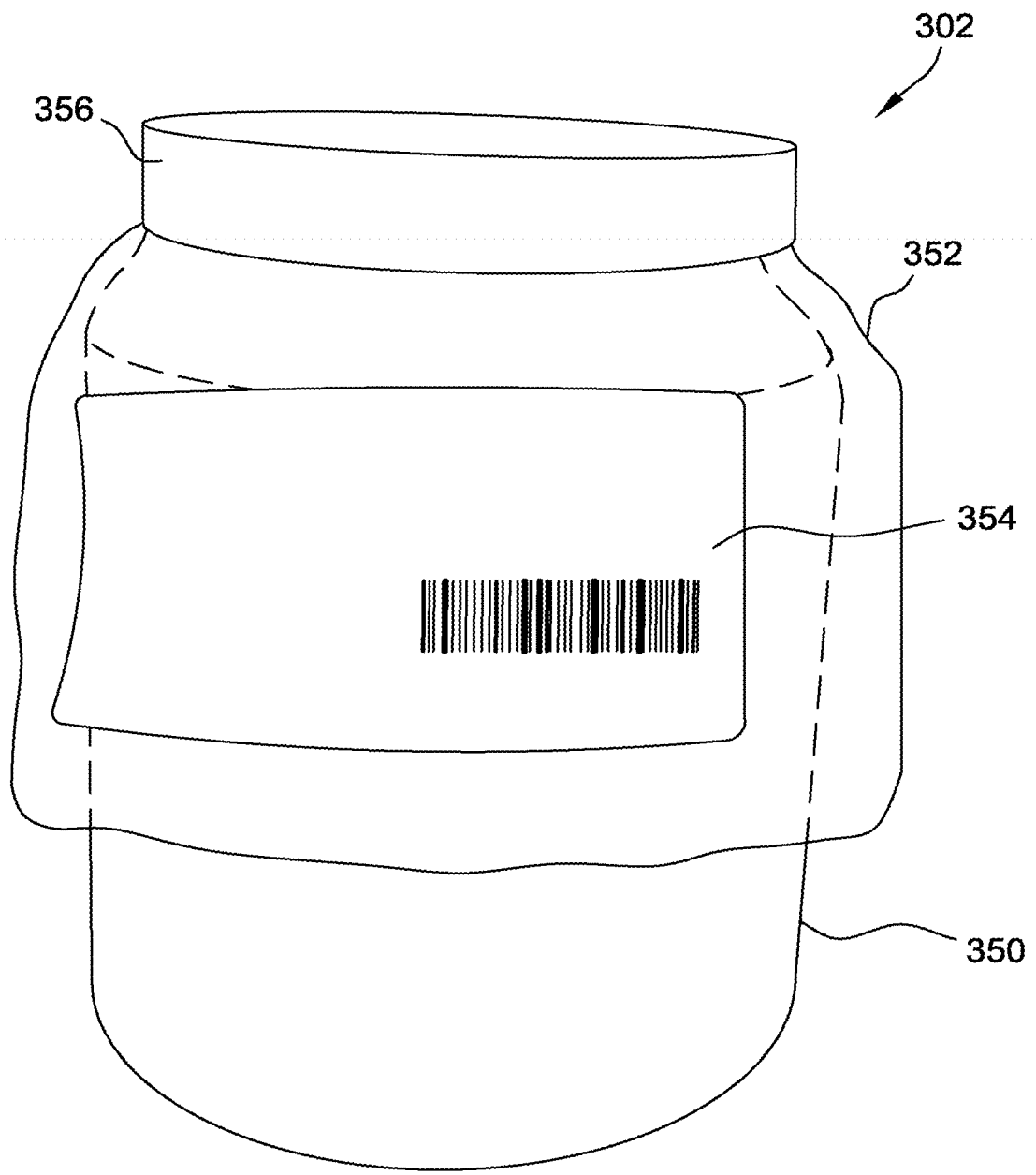
FIG. 7 is a front view of a bulk-up container for use with container disassembly workstation, according to an example embodiment.

FIGS. 3-6 include various views of a container disassembly workstation 125, according to an example embodiment. The disassembly workstation 125 may be deployed in the prescription order processing system 100 (shown in FIG. 1), or may otherwise be deployed. FIG. 3 is a perspective view of a container disassembly workstation 125. FIG. 4 is another perspective view of the container disassembly workstation 125 (shown in FIG. 3). FIG. 5 is a top view of the container disassembly workstation 125 (shown in FIG. 3). FIG. 6 is a front view of the container disassembly workstation 125 (shown in FIG. 3). FIG. 7 is a front view of a bulk-up container 302 for use with container disassembly workstation 125. FIGS. 3-6 includes a coordinate system 127 including an X-axis, a Y-axis, and a Z-axis for reference purposes to indicate an orientation of the various figures.

The container disassembly workstation 125 is generally configured to facilitate "bulking-up" of pharmaceuticals for filling orders in the prescription order processing system 100. In some embodiments, bulking-up includes receiving the containers of one or more than one container of a particular size or of various sizes of a particular type of drug in a specific container configured to facilitate easier dispensing. More specifically, container disassembly workstation 125 includes a base 200, a desktop 202, and a pharmaceutical receptacle assembly 204 configured to facilitate transferring pharmaceuticals contained within relatively small volume containers 300 (see FIG. 8) into relatively larger volume bulk containers 302 (see FIG. 7).

The desktop 202 is connected to the base 200 and defines a container disassembly workspace 206. In this embodiment, the desktop 202 is L-shaped. In some embodiments, the desktop 202 is one of linear, T-shaped, and U-shaped. Other shapes may also be used. A rotary storage device 208 is connected to an upper surface 216 of the desktop 202 and is configured to facilitate access by the operators to workstation accessories during operation of the container disassembly workstation 125. A pharmaceutical receptacle assembly 204 extends through a disassembly area 210 of the desktop 202 and a bulk container receptacle 212 configured to receive and retain a bulk container 302 positioned in a bulk container area 303 vertically below the pharmaceutical receptacle assembly 204. A container staging area 214 is defined along the upper surface 216 adjacent to the pharmaceutical receptacle assembly 204 and is configured to facilitate staging of the containers 300 for disassembly by the operators during operation of the container disassembly workstation 125.

The pharmaceutical receptacle assembly 204 includes a pharmaceutical dust separation screen 232, a pharmaceutical dust receptacle 234, and a pharmaceutical receptacle 236. In an example embodiment, the pharmaceutical receptacle 236 is positioned adjacent to the pharmaceutical dust receptacle 234 and the pharmaceutical duct separation screen 232 is positioned within a screen retention cavity 239 of the pharmaceutical dust receptacle 234. In some embodiments, the pharmaceutical receptacle assembly 204 may be arranged in any manner that facilitates operation of the container disassembly workstation 125 as described herein.

In an example embodiment, the pharmaceutical dust separation screen 232 is configured to retain the pharmaceuticals and to permit pharmaceutical dust to pass through the pharmaceutical dust separation screen 232 to enter the pharmaceutical dust receptacle 234. More specifically, pharmaceutical dust separation screen 232 includes holes 238 sized to facilitate pharmaceutical dust passing through the pharmaceutical dust separation screen 232 while facilitating retention of the pharmaceuticals against the pharmaceutical dust separation screen 232. In some embodiments, the pharmaceutical dust separation screen 232 is a stainless steel alloy. In some embodiments, the pharmaceutical dust separation screen 232 is any type of material and includes holes 238 of any size and configuration that facilitate separation of pharmaceutical dust from the pharmaceuticals during operation of the container disassembly workstation 125. For example, in one embodiment, the holes are 0.156 inches in diameter such that a small pill size of 0.187 does not fall through. In an example embodiment, pharmaceutical dust separation screen 232 is purchased with holes 238 and then modified and customized to fit specific workstations 125.

In an example embodiment a vacuum system 240 is connected to the pharmaceutical dust receptacle 234 and is configured to apply a vacuum to the pharmaceutical dust receptacle 234 to facilitate drawing pharmaceutical dust through the pharmaceutical dust separation screen 232 and into the funnel-shaped pharmaceutical dust receptacle 234. In this embodiment, the pharmaceutical dust is stored in a dust bucket 242 proximate each container disassembly workstation 125. In some embodiments, the vacuum system 240 includes a centralized dust collection apparatus (not shown) coupled in flow communication with multiple container disassembly workstations 125.

The pharmaceutical receptacle 236 includes a pharmaceutical receptacle funnel 246 configured to receive the pharmaceuticals from the pharmaceutical dust separation screen 232 and a door 244 suitably connected, e.g., by hinges, to the pharmaceutical receptacle funnel 246. The door 244 is configured to be moved between a closed position in which pharmaceuticals are inhibited from entering the pharmaceutical receptacle funnel 246 and an open position in which the pharmaceuticals can be transferred from the pharmaceutical dust separation screen 232 into the pharmaceutical receptacle funnel 246. The pharmaceuticals are then directed by the pharmaceutical receptacle funnel 246 into one bulk container 302. In some embodiments, the pharmaceutical receptacle 236 includes any components in any configuration that facilitates the operation of container disassembly workstation 125 as described herein.

With reference to FIGS. 3-6, the base 200 is shown in an embodiment to extend along the Z-direction by a height 218 and is connected to a desktop bottom surface 220. In certain embodiments, glove receptacles 222, a refuse receptacle 226, and/or leveling feet 228 may be affixed to the container disassembly workstation 125 to facilitate ease of use by the operator. The glove receptacles 222 are connected to an outer face 224 of base 200 and are configured to retain gloves for use by the operators. The refuse receptacle 226 is connected to bottom surface 220 and is configured to receive and retain a refuse bag. The leveling feet 228 are connected to base 200 and are configured to facilitate leveling of the desktop 202 by providing elevation adjustments at multiple points along a vertically lower portion 230 of the base 200. In other embodiments, the base 200 may include any components in any arrangement that facilitates operation of the container disassembly workstation 125 as described herein.

FIG. 7 is a front view of a bulk container 302, according to an example embodiment. The bulk container 302 may be used in conjunction with the container disassembly workstation 125, or may otherwise be used. The bulk container 302 is shown to include a rigid container 350 and a flexible bag 352 that fits inside the rigid container 350. A label 354 is affixed to the flexible bag 352 and includes all of the pharmaceutical's relevant identifying information and barcodes. A lid 356 can be screwed onto the rigid container 350 with the flexible bag 352 being between the lid 356 and the rigid container 350, as shown in FIG. 7. In the example embodiment, the bulk container 302 is a one gallon container. However, different sized containers may be used. For example, a half-gallon container or a two gallon container may be used. Once filled with drug, the bulk containers 302 are transported to another location (e.g., a central location) within the prescription order processing system 100 to facilitate further distribution of the pharmaceuticals during operation of the prescription order processing system 100.

Figure 8:
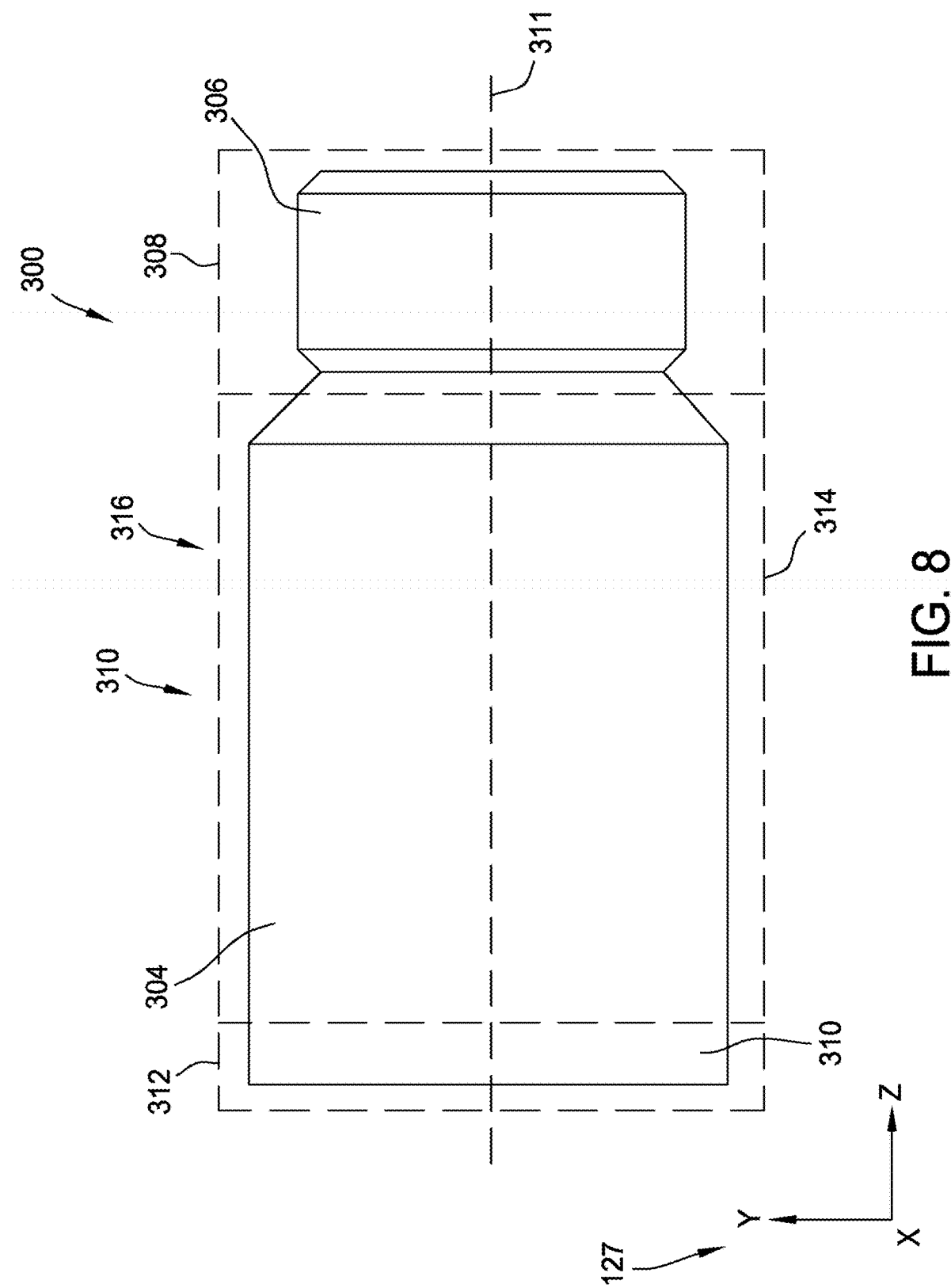
FIG. 8 is a front view of a container that may be used with the container disassembly workstation shown in FIG. 3, according to an example embodiment.

FIG. 8 is a front view of a container 300 that may be used with the container disassembly workstation 125 (shown in FIG. 3). In this embodiment, the containers 300 are cylindrical hollow bottles having a body 304 and a lid 306. The body 304 includes a top 308 and a base 310, the top 308 being threaded to receive the lid 306 to facilitate retaining pharmaceuticals within the container 300. A first portion 312 of the container 300 and a second portion 314 of the container 300 are defined as illustrated in FIG. 7. In this embodiment, the containers 300 are fabricated from a high-density polyethylene (HDPE) material. In some embodiments, the containers 300 are fabricated from at least one of polyethylene terephthalate (PET), #2 plastic, and #5 plastic. In additional embodiments, the containers 300 may have any shape and configuration that facilitates operation of the prescription order processing system 100 as defined herein.

Figure 9:
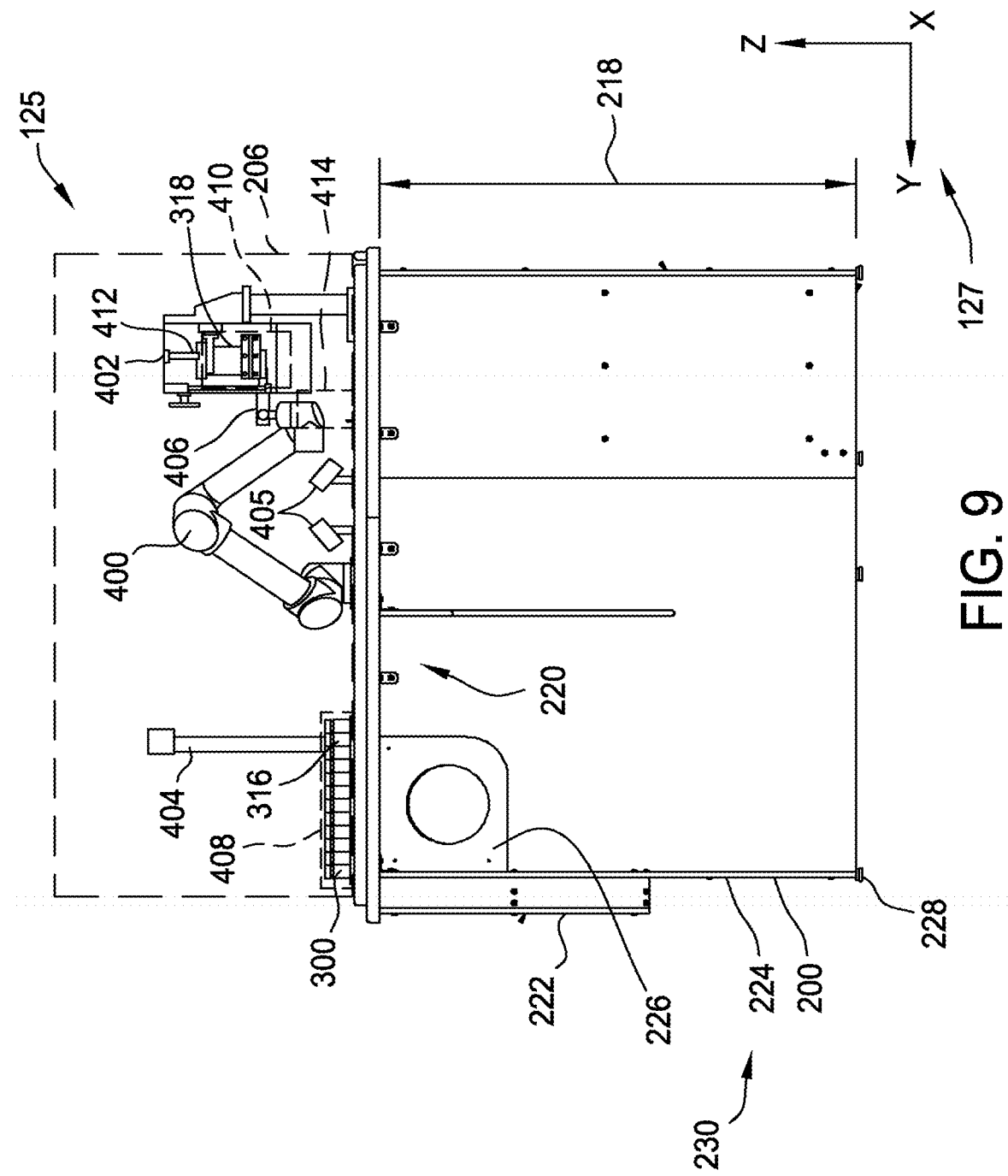
FIG. 9 is a front view of an embodiment of the container disassembly workstation shown in FIG. 3 illustrating a container manipulation device, a cutter device, and a scanner, according to an example embodiment.

FIG. 9 is a front view of an example embodiment of the container disassembly workstation 125. The container disassembly workstation 125 may be deployed in the prescription order processing system 100, or may otherwise be deployed.

In an embodiment shown in FIG. 9, the container disassembly workstation 125 includes a container manipulation device 400, a cutter device 402, a container height scanner device 404, and a container barcode scanner device 405. The container disassembly workstation 125 as shown in FIG. 9 includes a substantial number of similar elements to the container disassembly workstation 125 shown in FIGS. 3-6. The container disassembly workstation 125 of FIG. 9 further includes the container manipulation device 400, the cutter device 402, and the scanner devices 404 and 405 connected to the container disassembly workstation 125. The elements 400, 402, 404, 405 are utilized to disassemble the containers 300 and to process the pharmaceuticals contained therein.

In an example embodiment, the container manipulation device 400 includes a gripper 406 that is configured to grip and move one container 300 between at least a first position 408 proximate the container height scanner device 404 and a second position 410 proximate the cutter device 402 within the container disassembly workspace 206. The gripper 406 includes a pair of textured fingers that open and close to grasp and release the containers 300. The container height scanner device 404 is configured to sense the height of the container 300 to determine the presence of at least one container 300 positioned in the first position 408. The cutter device 402 includes a cutter head 412 configured to cut through a wall of the container 300 to separate the first portion 312 of the container 300 from the second portion 314 of the container 300 when the container 300 is in the second position 410. In an example embodiment, the cutter head 412 is one of a blade or an ultrasonic device. Generally, the cutter head 412 is any device that facilitates cutting the container 300. The container barcode scanner device 405 is positioned between the first position 408 and the second position 410, proximate the container manipulation device 400, and scans the barcode on each container 300 to verify that the container has the correct barcode associated with the work order that generates the number of containers 300 needed to fill the bulk container 302.

More specifically, during operation of the container disassembly workstation 125, the container manipulation device 400 is configured to grip the first portion 312 of the container in a first, upright orientation 316 at the first position 408 such that a container longitudinal axis 311 is substantially aligned with the Z-direction and the lid 306 is vertically higher with respect to the Z-direction than the base 310. The container manipulation device 400 is also configured to move the container 300 from the first position 408 to the second position 410, and orient the container 300 in a second, upside-down orientation 318 at the second position. The container manipulation device 400 is further configured to move the first portion 312 of the container 300 from the second position 410 to a third position 414, wherein the third position 414 is vertically above the pharmaceutical dust separation screen 232, and finally, to orient the container 300 in the second orientation 318, thereby completing the transfer of the pharmaceuticals from the container 300 to the pharmaceutical receptacle assembly 204. In some embodiments, a chute or funnel is used to transition the pharmaceuticals from a behind an enclosed structure to a non-enclosed pharmaceutical dust separation screen 232 that allows for continuous operation of workstation 125.

Figure 10:
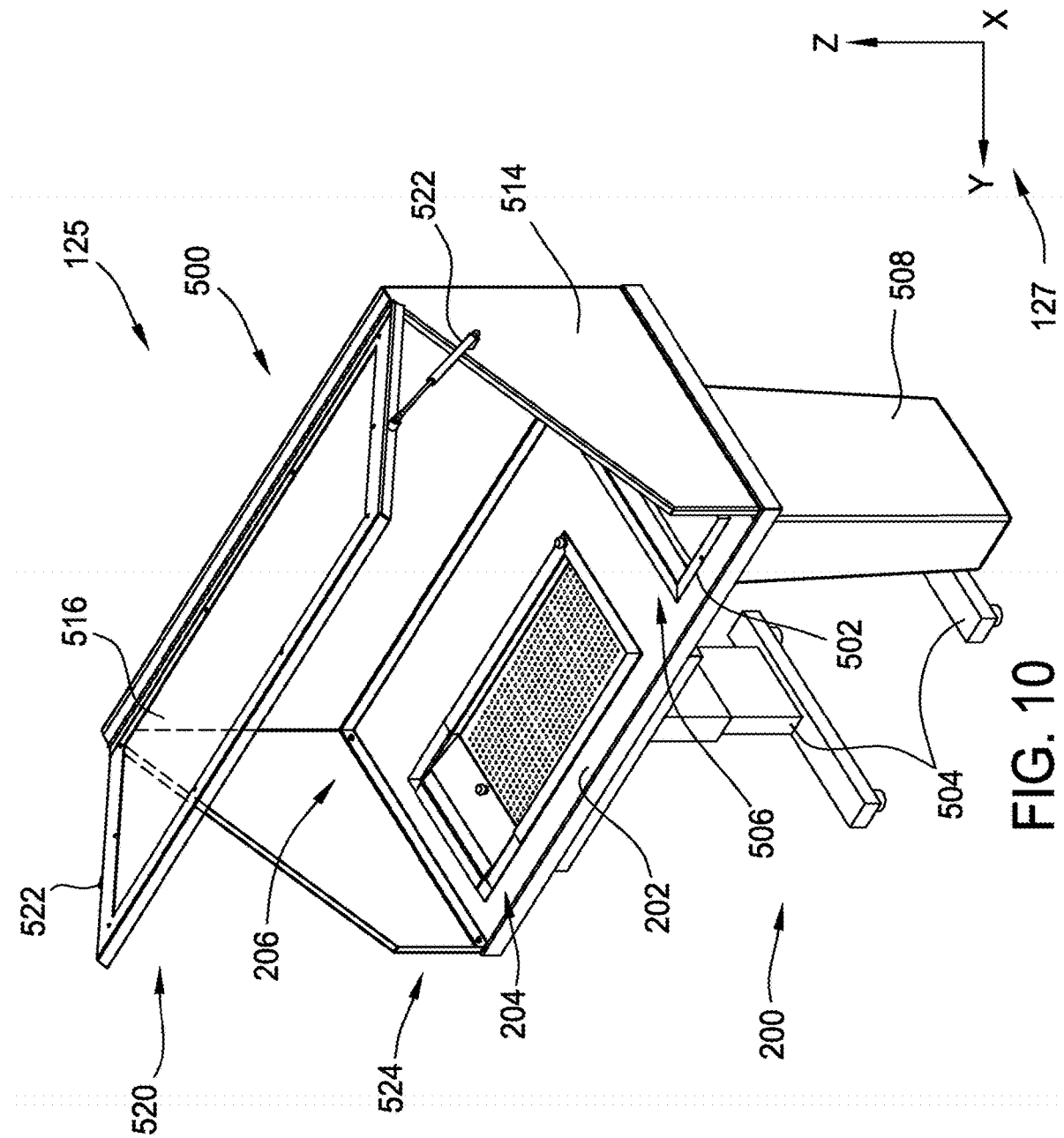
FIG. 10 is a perspective view of an embodiment of the container disassembly workstation shown in FIG. 3 illustrating a shielded adjustable height container disassembly workstation, according to an example embodiment.
Figure 11:
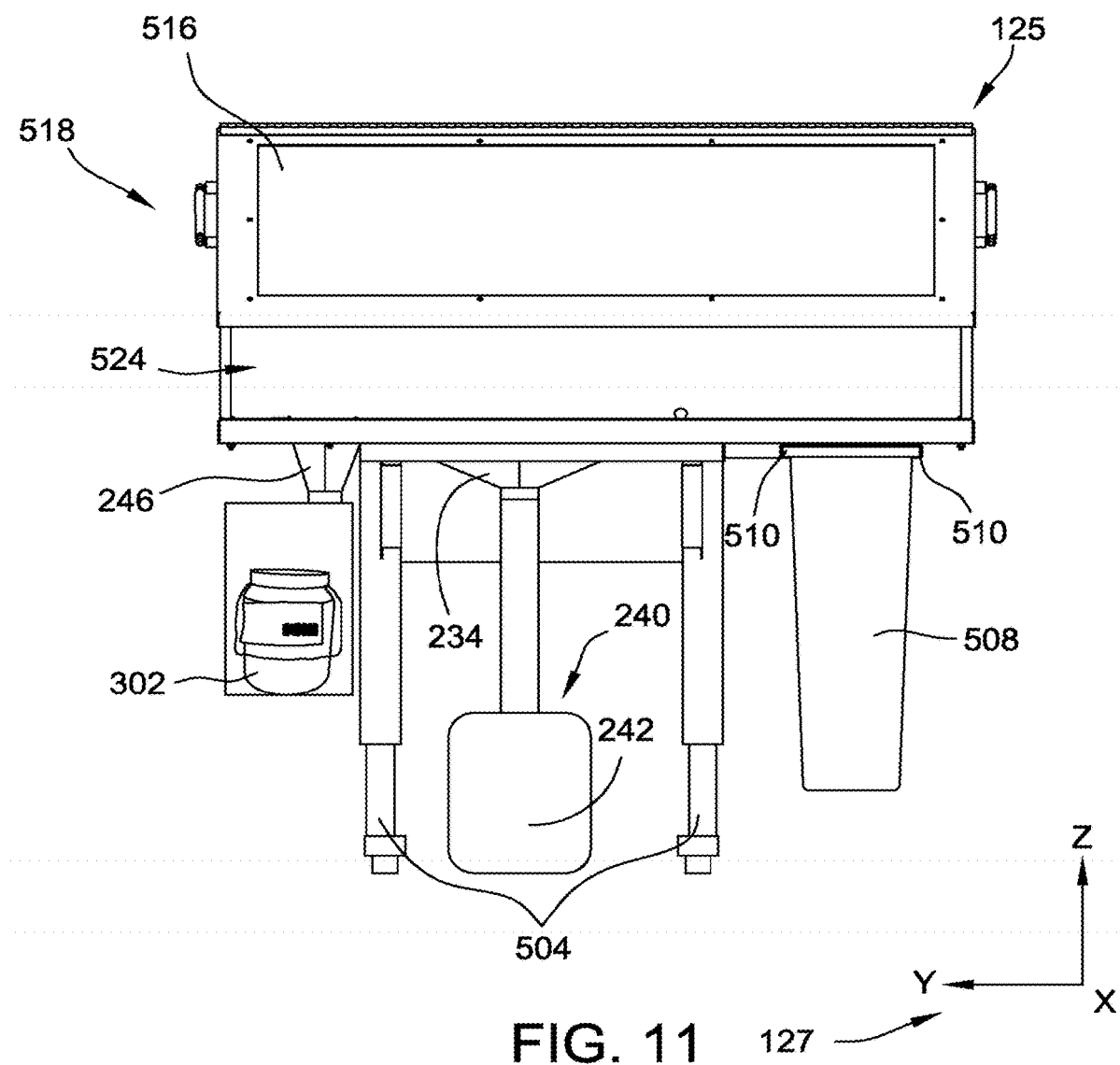
FIG. 11 is a front view of an embodiment of the container disassembly workstation shown in FIG. 10, according to an example embodiment.
Figure 12:
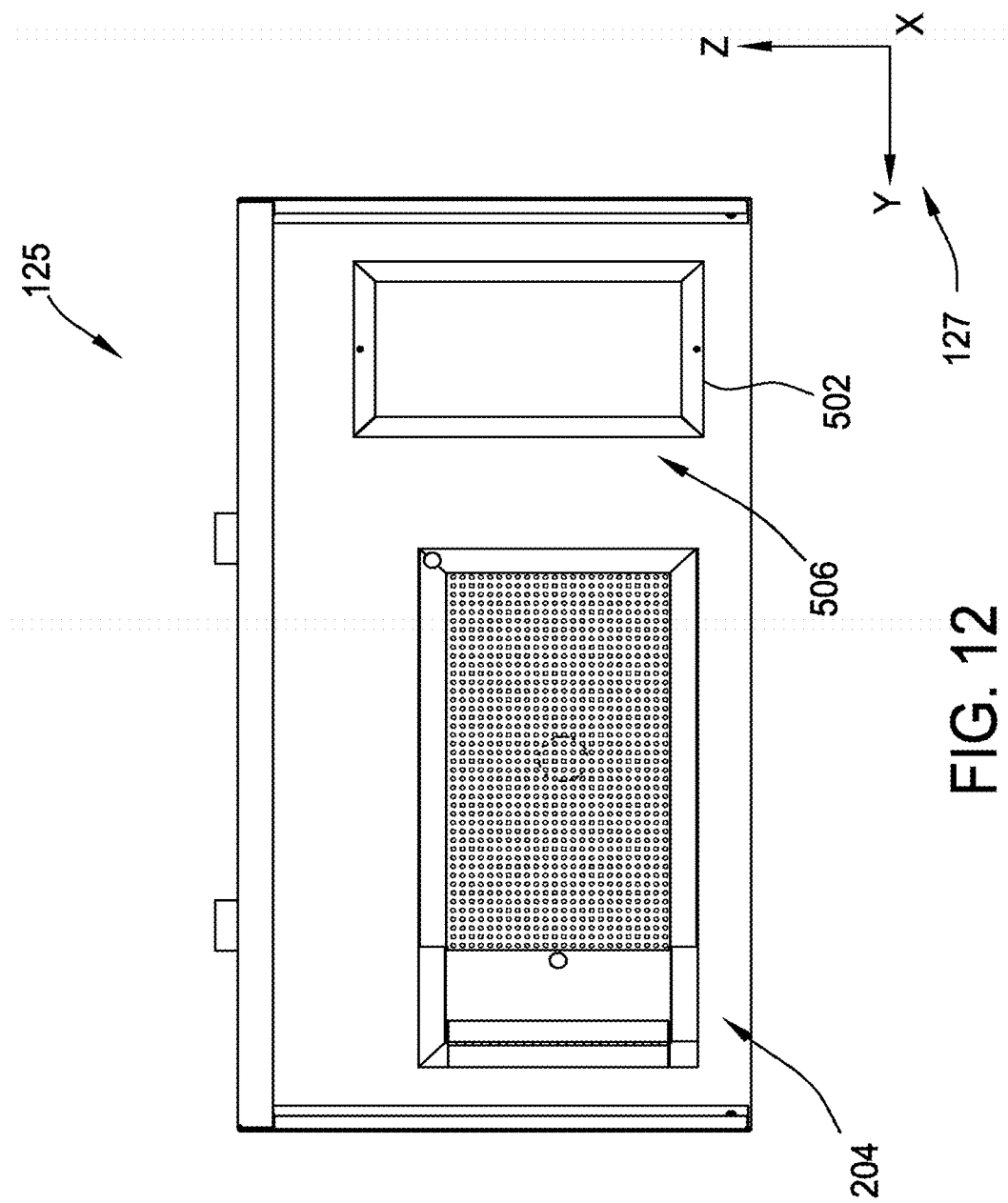
FIG. 12 is a top view of an embodiment of the container disassembly workstation shown in FIG. 10, according to an example embodiment.
Figure 13:
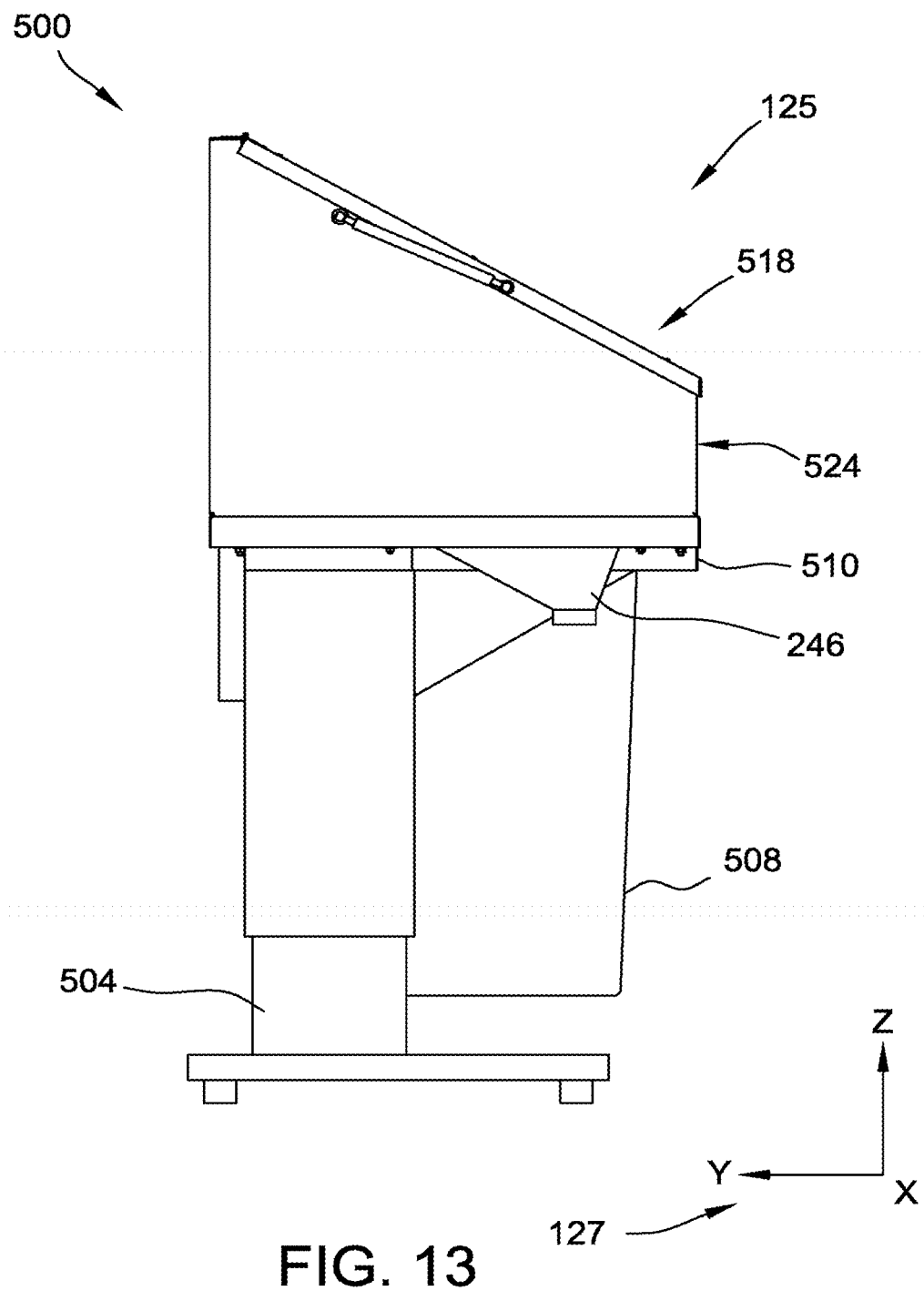
FIG. 13 is a side view of an embodiment of the container disassembly workstation shown in FIG. 10, according to an example embodiment.

FIGS. 10-13 include various views of a container disassembly workstation 125, according to an example embodiment. The disassembly workstation 125 may be deployed in the prescription order processing system 100 (shown in FIG. 1), or may otherwise be deployed. FIG. 10 is a perspective view of an embodiment of the container disassembly workstation 125. FIG. 11 is a front view of an embodiment of the container disassembly workstation 125. FIG. 12 is a top view of an embodiment of the container disassembly workstation 125. FIG. 13 is a side view of an embodiment of the container disassembly workstation 125. The embodiment of the container disassembly workstation 125 shown in FIGS. 10-13 includes substantially similar components to the container disassembly workstation 125 shown in FIGS. 3-6 except that the container disassembly workstation 125 of FIGS. 9-12 includes an adjustable base 200, a shield assembly 500, and a container receptacle 502. In some embodiments, the adjustable base 200 may provide for easier usage by operators of various heights and performing various duties. In some embodiments, the shield assembly 500 may provide increased protection and/or safety to operators that are handling pharmaceuticals with strong smells, to which a person may have an adverse reaction by handling the pharmaceuticals or inhaling smells associated with the pharmaceuticals, or otherwise.

The adjustable base 200 includes a pair of height adjustable legs 504 configured to facilitate movement of the desktop 202 along the Z-direction to operational positions between a high position and a low position to facilitate ergonomic placement of the desktop 202 relative to the operators. The container receptacle 502 defines a container receptacle opening 506 in the desktop 202 that is sized to receive at least a portion of the pharmaceutical containers 300. In an example embodiment, the container receptacle 502 includes a scrap bin 508 configured to receive emptied and disassembled containers 300. The desktop 202 includes a rail system 510 coupled to the bottom side 220 of the desktop 202 and extending along at least two sides of the container receptacle opening 506. The rail system 510 is configured to facilitate retention and removal of the scrap bin 508.

The shield assembly 500 is connected to the desktop 202 and is configured to at least partially shield an operator (shown in FIG. 2) from the container disassembly workspace 206. The shield assembly 500 includes a shield frame 514 connected to the desktop 202 and an access door 516 moveably connected to the shield frame 514. In an example embodiment, the access door 516 is rotatably connected to the shield frame 514 and is moveable between a closed position 518 and an open position 520. The open position 520 facilitates access to the container disassembly workspace 206 by the operators and the closed position 518 inhibits access to the container disassembly workspace 206 by the operators. A pair of biasing members 522 are connected between the shield frame 514 and the access door 516 and are configured to assist moving the access door 516 between the closed position 518 and the open position 520. In some embodiments, the biasing members 522 are gas charged struts. In some embodiments, the biasing members 522 are spring-assist struts.

In some embodiments, the shield frame 514 is stainless steel, the access door 516 is a substantially transparent acrylic material, and an access gap 524 is defined between the desktop 202 and an end of the access door 516. In some embodiments, at least a portion of the access door 516 translucent, opaque, and/or solid. In some other embodiments, the container disassembly workstation 125 does not include the access gap 524. In some embodiments, a pair of operator gloves are integral to the shield frame 514 and that are configured to receive an operator's hands and arms extend through at least a portion of the shield frame 514 such that an operator is able to interact with the container disassembly workspace 206 without being directly exposed to the container disassembly workspace 206. In some embodiments, the desktop 202, the shield frame 514, and/or the access door 516 are configured to inhibit radiation from passing through the desktop 202, the shield frame 514, and/or the access door 516. In some embodiments, a vacuum system, such as vacuum system 240, is connected in flow communication with container disassembly workspace 206.

Figure 14:
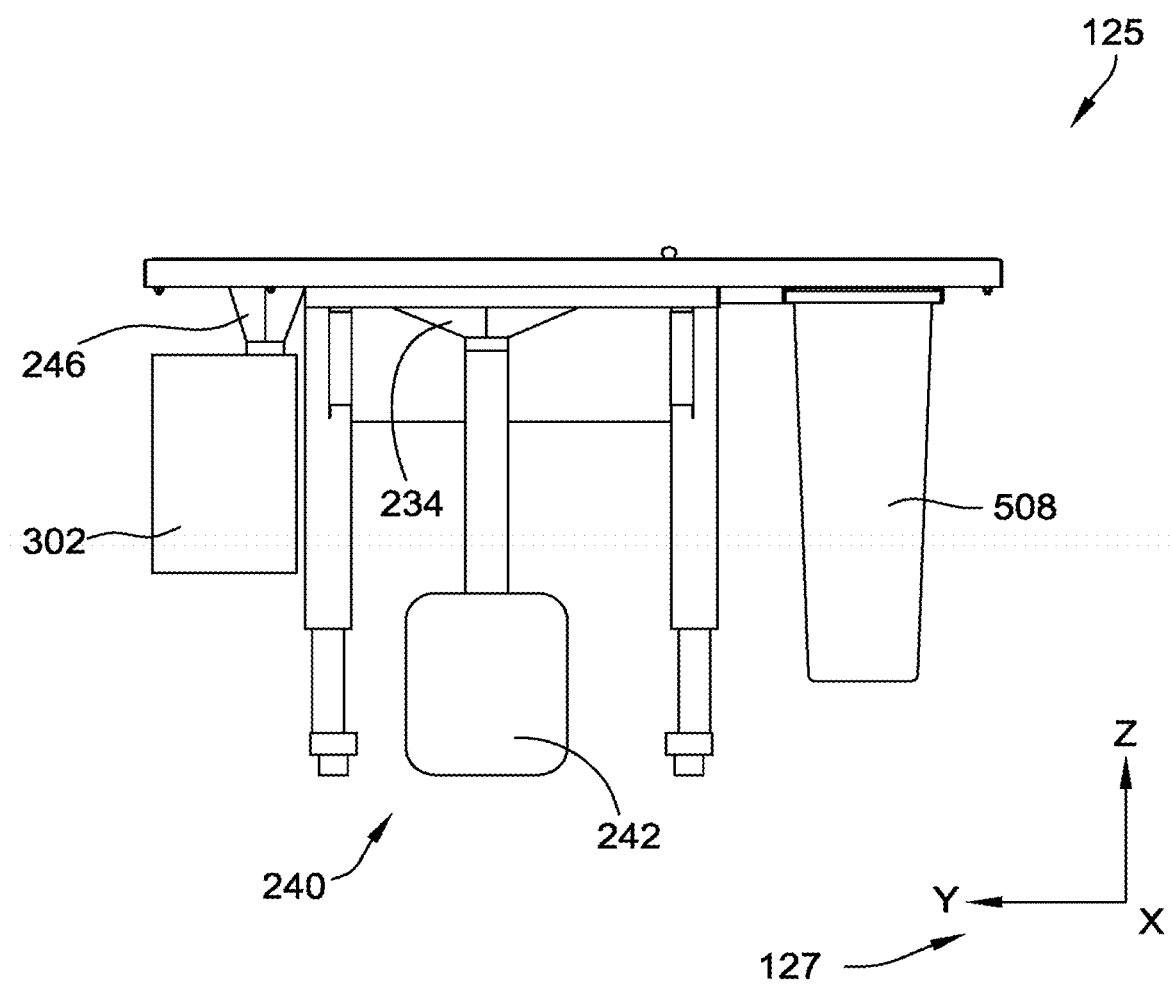
FIG. 14 is a front view of an embodiment of the container disassembly workstation shown in FIG. 3 illustrating a non-shielded adjustable height container disassembly workstation, according to an example embodiment.
Figure 15:
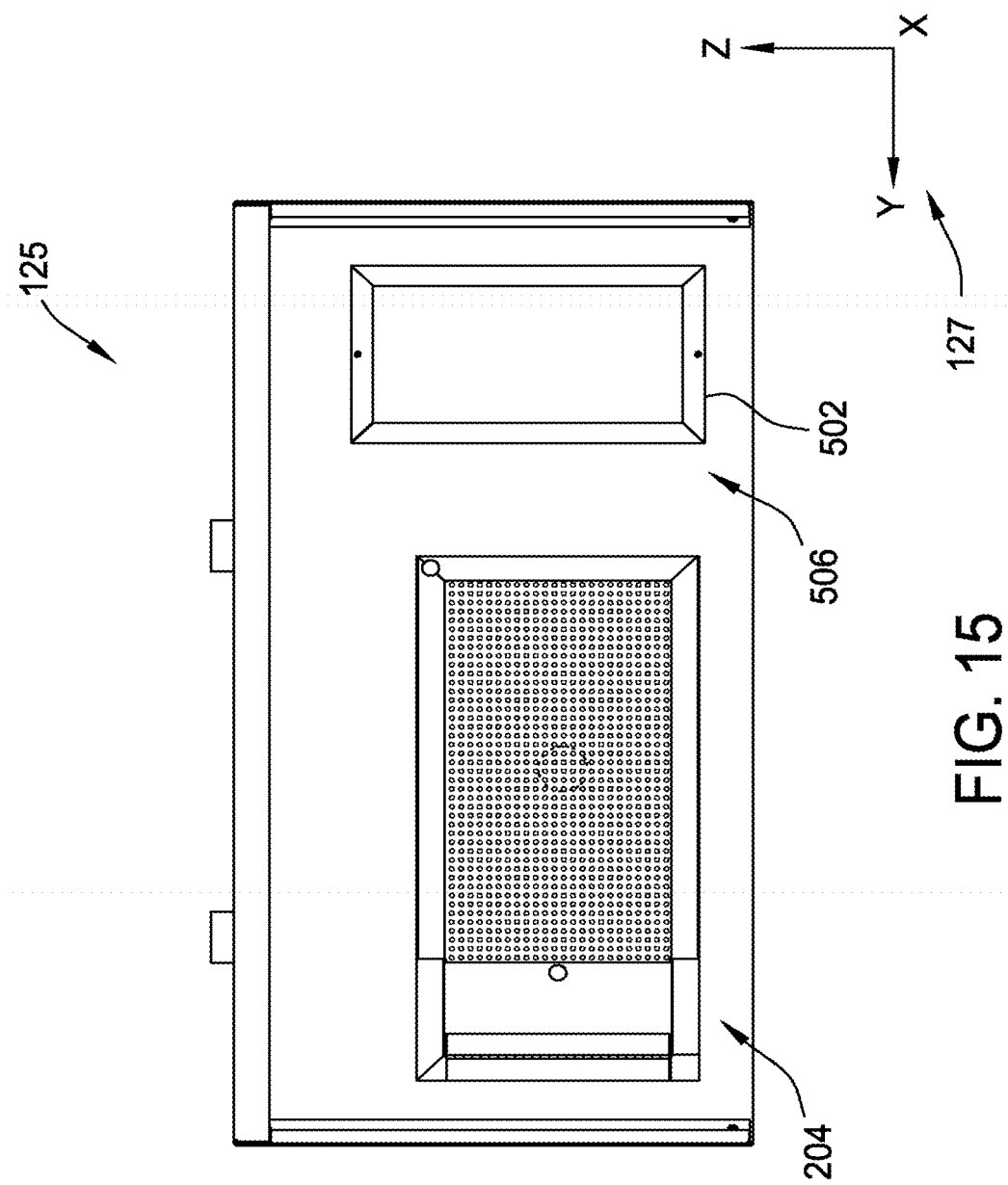
FIG. 15 is a top view of an embodiment of the container disassembly workstation shown in FIG. 14, according to an example embodiment.

FIGS. 14 and 15 includes several views of a container disassembly workstation 125, according to an example embodiment. The disassembly workstation 125 may be deployed in the prescription order processing system 100 (shown in FIG. 1), or may otherwise be deployed. FIG. 14 is a front view of an embodiment of the container disassembly workstation 125. FIG. 15 is a top view of the third alternative embodiment of the container disassembly workstation 125. The container disassembly workstation 125 shown in FIGS. 14 and 15 include substantially the same elements as the container disassembly workstation 125 shown in FIGS. 10-13 except that the container disassembly workstation 125 shown in FIGS. 14 and 15 does not include the shield assembly 500. In some embodiments, the container disassembly workstation 125 may be used to provide a compact container disassembly workstation 125 that facilitates easy adjustment for a wide variety of usage in a prescription order processing system.

Figure 16:
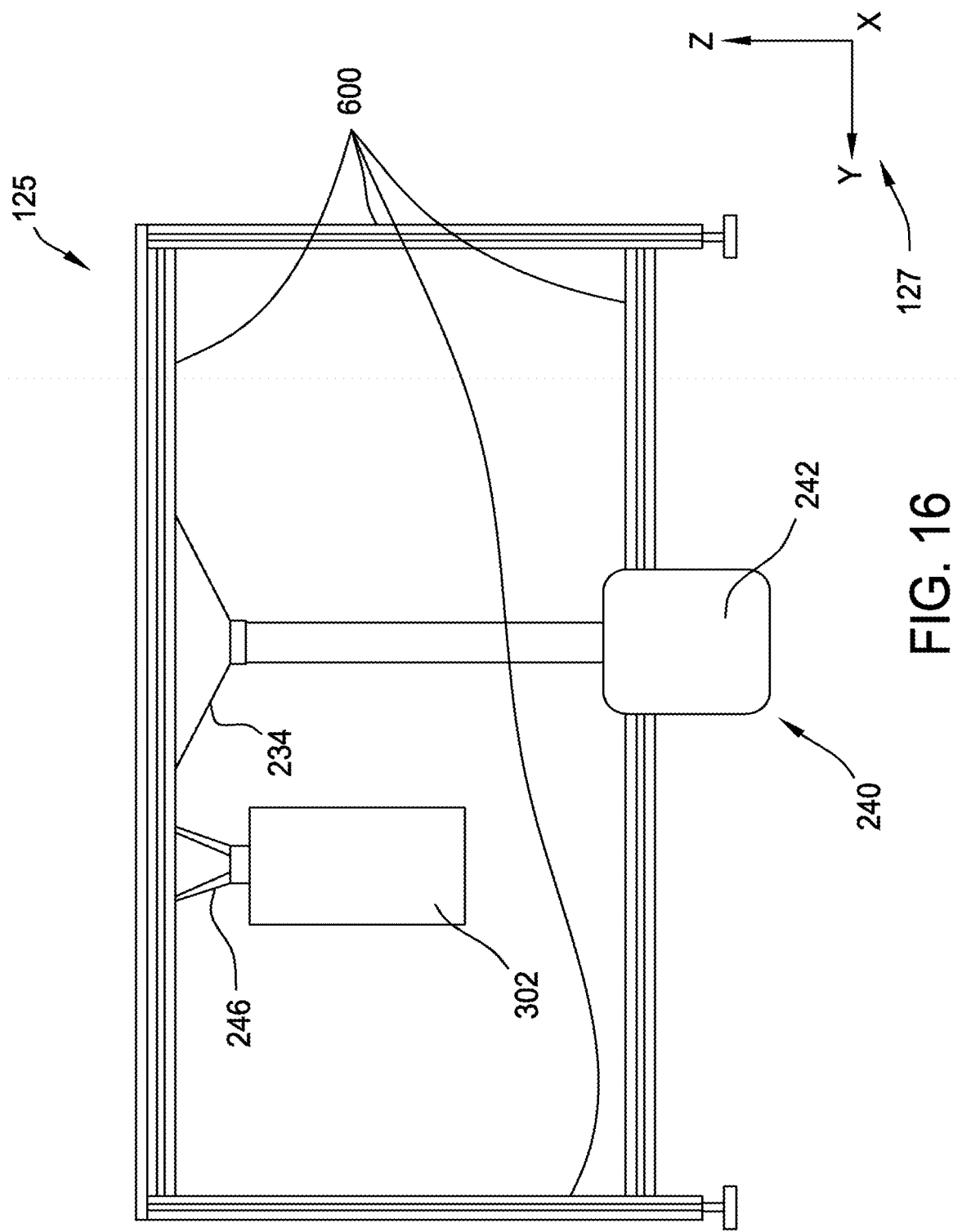
FIG. 16 is a front view of an embodiment of the container disassembly workstation shown in FIG. 3 illustrating a modular container disassembly workstation, according to an example embodiment.

FIG. 16 is a front view of an embodiment of the container disassembly workstation 125 illustrating a modular container disassembly workstation 125, according to an example embodiment. The container disassembly workstation 125 shown in FIG. 16 includes substantially similar elements to the container disassembly workstation 125 shown in FIGS. 3-6 except that the base 200 of the container disassembly workstation 125 of FIG. 16 is formed from a modular building material 600 configured to be expediently assembled together without the need for custom fabrication or specialty tools.

Figure 17:
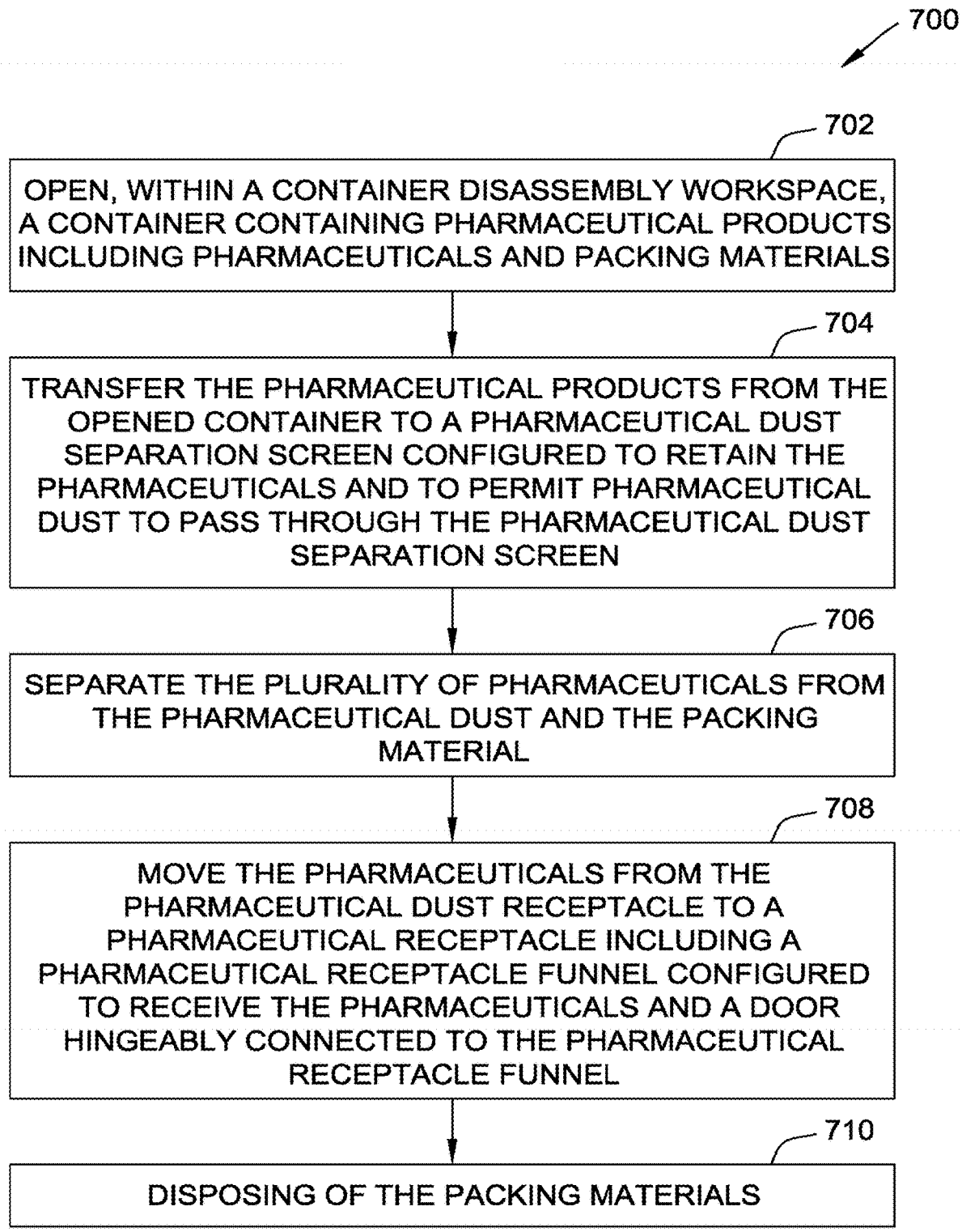
FIG. 17 is an example process flow illustrating a method for disassembly containers using a container disassembly workstation, according to an example embodiment.

FIG. 17 is an example process flow illustrating a method 700 for container disassembly, according to an example embodiment. The method 700 may be performed on a container 300 that contains pharmaceuticals using a container disassembly workstation 125, or may otherwise be performed.

At block 702, the container 300 that contains pharmaceutical products including pharmaceuticals and packing materials is opened within a container disassembly workspace 206 of the container disassembly workstation 125.

At block 704, the pharmaceutical products are transferred from the opened container 300 to a pharmaceutical dust separation screen 232 of a pharmaceutical receptacle assembly 204. In general, the pharmaceutical dust separation screen 232 is configured to retain the pharmaceuticals and to permit pharmaceutical dust to pass through the pharmaceutical dust separation screen 232.

The pharmaceuticals are separated from the pharmaceutical dust and the packing materials at block 706.

At block 708, the pharmaceuticals are moved from the pharmaceutical dust receptacle screen 232 to a pharmaceutical receptacle 236. In some embodiments, the pharmaceutical receptacle 236 includes a pharmaceutical receptacle funnel 246 configured to receive the pharmaceuticals from the pharmaceutical dust separation screen 232 and a door 244 suitably connected, e.g., by hinges, to the pharmaceutical receptacle funnel 246 and configured to move between an open position and a closed position.

The packing materials are disposed of at block 710.

Figure 18:
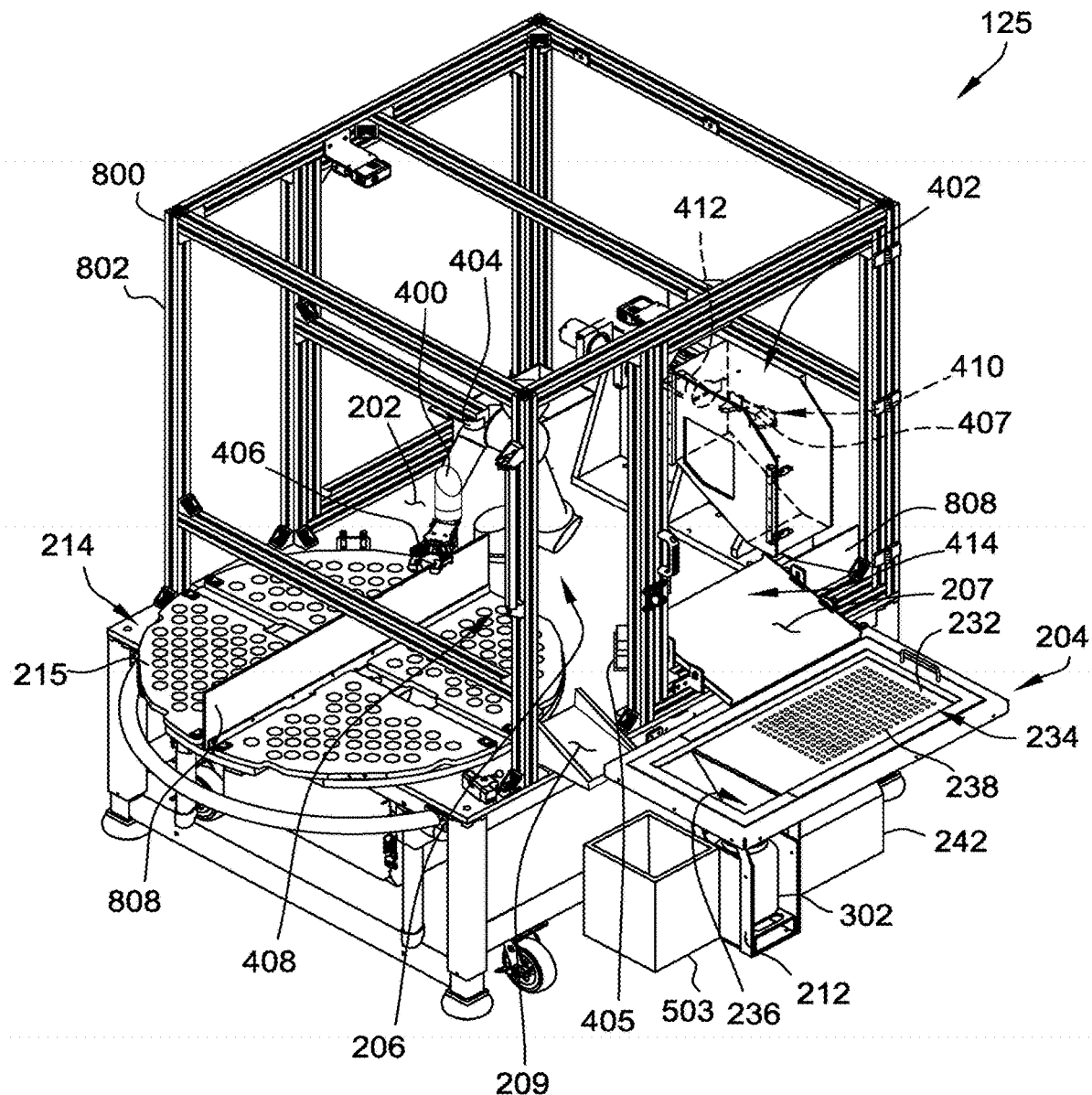
FIG. 18 is a perspective front view of an embodiment of the container disassembly workstation shown in FIG. 3 illustrating an enclosed container disassembly workstation, according to an example embodiment.
Figure 19:
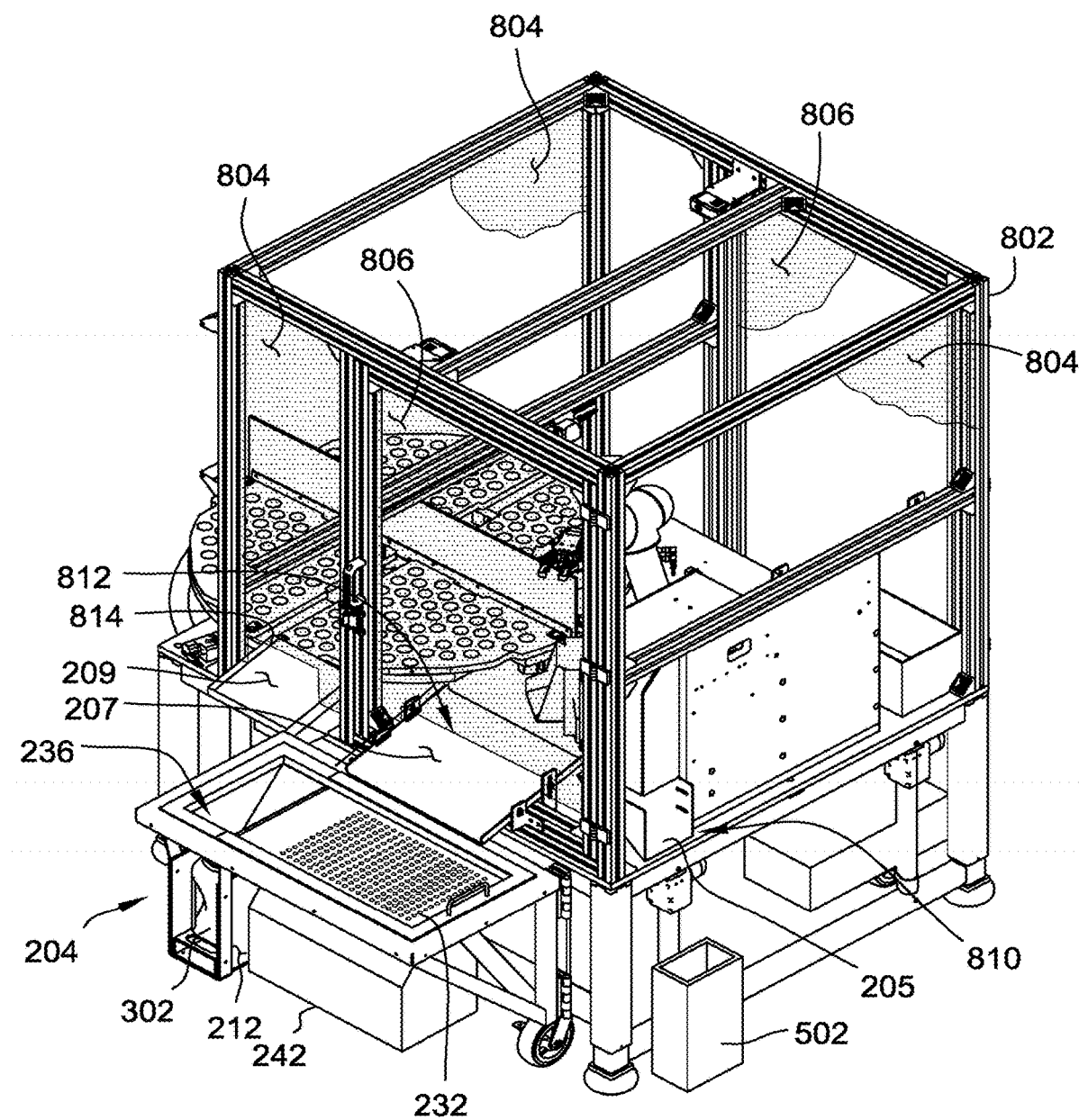
FIG. 19 is a perspective side view of an embodiment of the container disassembly workstation shown in FIG. 18, according to an example embodiment.
Figure 20:
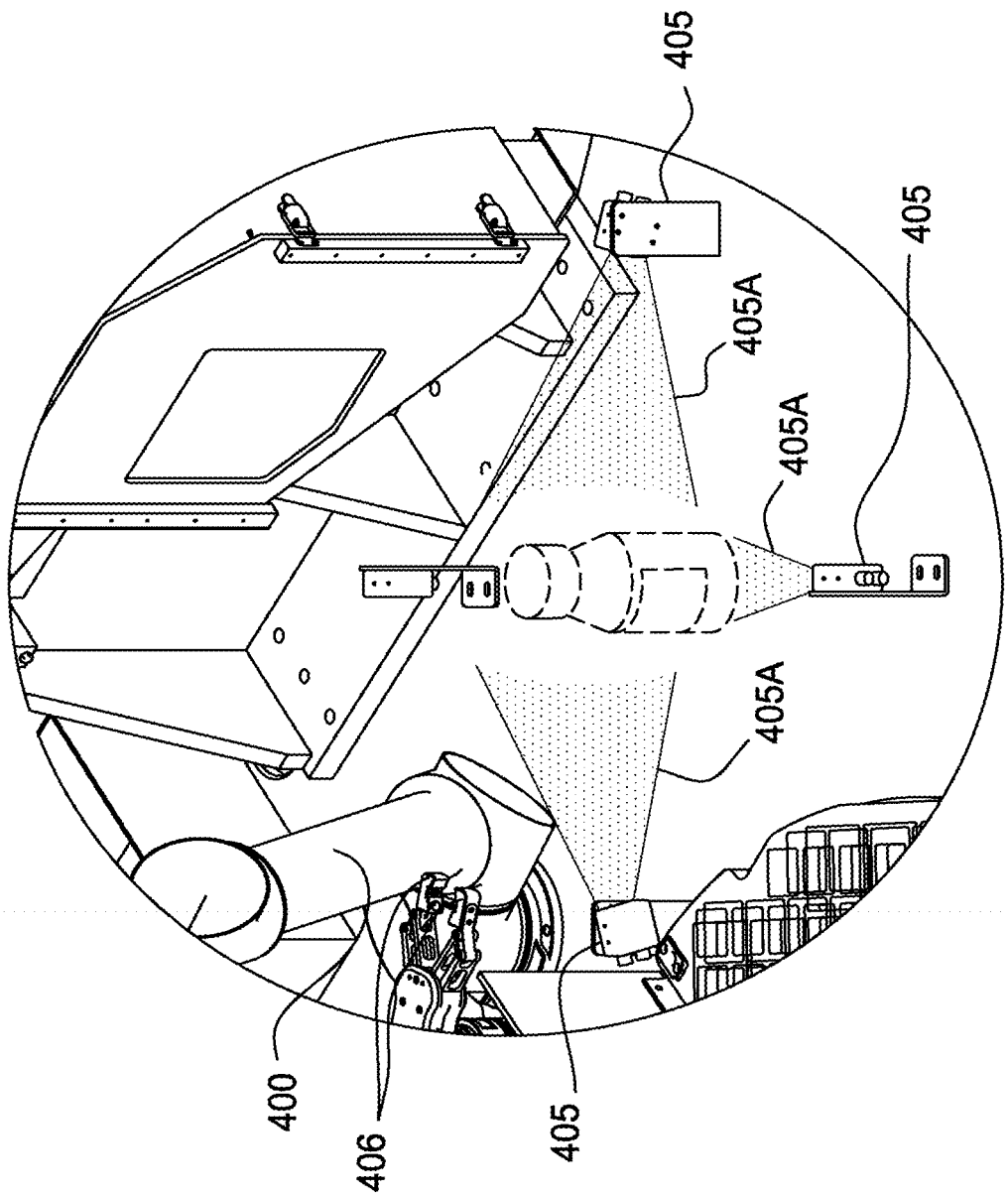
FIG. 20 is an enlarged view of a portion of the container disassembly workstation shown in FIG. 18.
Figure 21:
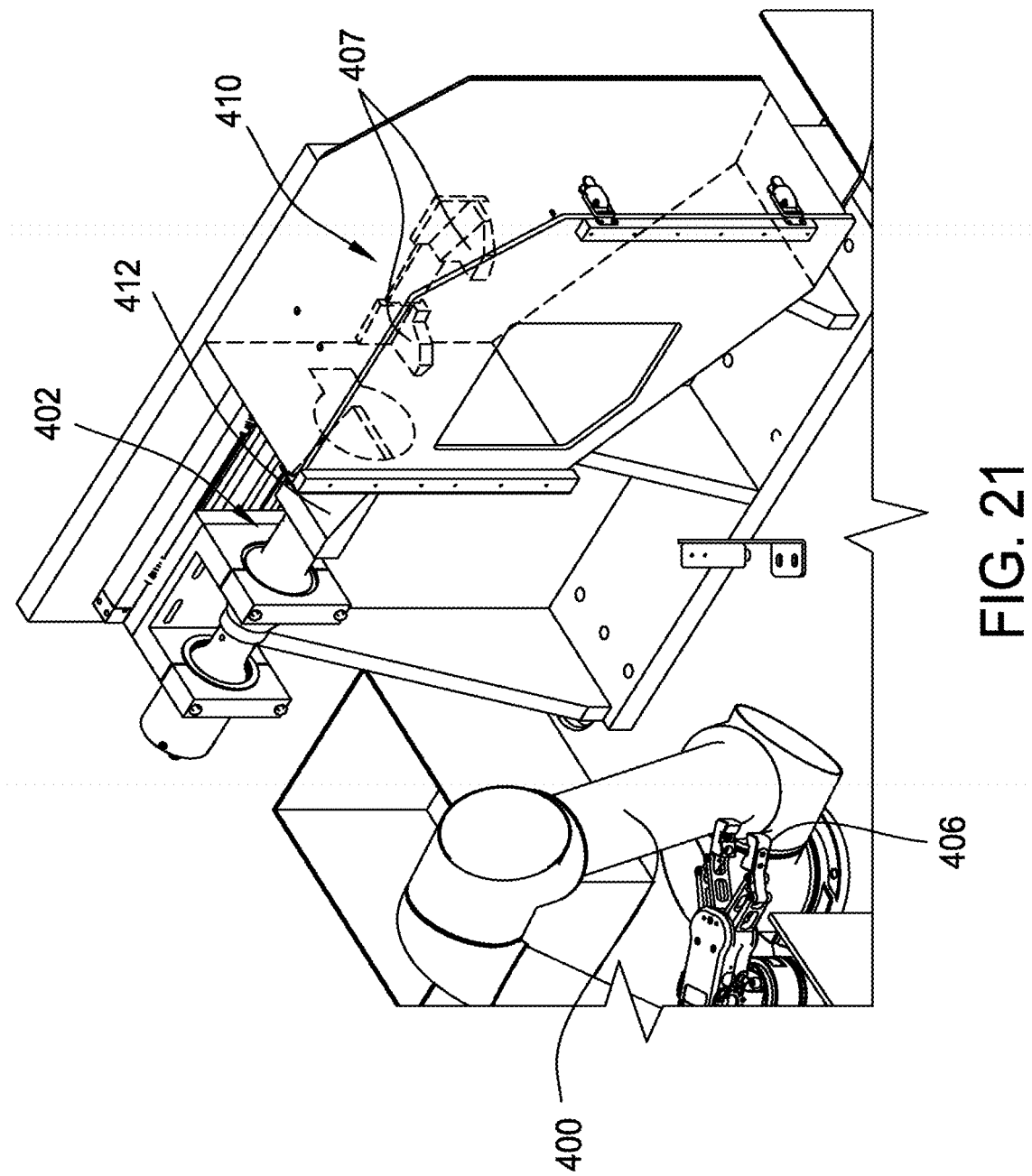
FIG. 21 is an enlarged view of another portion of the container disassembly workstation shown in FIG. 18.

FIGS. 18-21 includes various views of a container disassembly workstation 125, according to an example embodiment. The disassembly workstation 125 may be deployed in the prescription order processing system 100 (shown in FIG. 1), or may otherwise be deployed. FIG. 18 is a perspective front view of another embodiment of the container disassembly workstation shown in FIG. 3 illustrating an enclosed container disassembly workstation, and FIG. 19 is a perspective side view of the enclosed container disassembly workstation shown in FIG. 18. FIG. 20 is an enlarged view of a portion of the container disassembly workstation shown in FIG. 18. FIG. 21 is an enlarged view of another portion of the container disassembly workstation shown in FIG. 18. The embodiment of the container disassembly workstation 125 shown in FIGS. 18 and 19 includes the container manipulation device 400 and cutter device 402 of workstation 125 shown in FIG. 9 and also a shield assembly 800 similar to that of the workstation shown in FIG. 10.

The container disassembly workstation 125 of FIGS. 18-21 as illustrated includes a base 200, a desktop 202, and a pharmaceutical receptacle assembly 204 configured to facilitate transferring pharmaceuticals contained within relatively small volume containers 300 (see FIG. 8) into relatively larger volume bulk containers 302 (see FIG. 7). After receiving pharmaceuticals, the bulk containers 302 are, in some embodiments, transported to a central location within the prescription order processing system 100 to facilitate further distribution of the pharmaceuticals during operation of the prescription order processing system 100.

The desktop 202 is connected to the base 200 to define a container disassembly workspace 206. A container staging area 214 is defined along desktop 202 and is configured to facilitate staging of the containers 300 for disassembly by the container manipulation device 400 and the cutter device 402 during operation of the container disassembly workstation 125. The container staging area 214 includes a rotating plate 215 connected to the desktop 202 and onto which an operator can position containers 300 for rotating into the container disassembly workspace 206.

The shield assembly 800 is connected to the desktop 202 and is configured to at least partially shield an operator (shown in FIG. 2) from the container disassembly workspace 206. The shield assembly 800 includes a shield frame 802 connected to the desktop 202, multiple protective panels 804 connected to the shield frame 802 to isolate the operator from the container disassembly workspace 206, and at least one access door 806 moveably connected to the shield frame 802. In this embodiment, the access doors 806 are rotatably connected to the shield frame 802 and are moveable between a closed position and an open position to selectively facilitate access to the container disassembly workspace 206 by the operators.

In some embodiment, the shield frame 802 is stainless steel, the panels 804 and access doors 806 are made of a substantially transparent acrylic material. In some embodiments, at least a portion of the panels 804 are at least one of translucent, opaque, and solid. In some embodiments, gloves that are integral to the shield frame 802 and are configured to receive an operator's hands and arms extend through at least a portion of the shield frame 802 such that an operator is able to interact with the container disassembly workspace 206 without being directly exposed to the container disassembly workspace 206. In some embodiments, at least one of the desktop 202, the shield frame 802, panels 804, and the access doors 806 are configured to inhibit potentially harmful substances in the pharmaceutical from passing through at least one of the desktop 202, the shield frame 802, panels 804, and the access doors 806 to the operator. In some embodiments, a vacuum system, such as vacuum system 240, is connected in flow communication with container disassembly workspace 206. In some embodiments, the container disassembly workspace 206 may not be accessed by the operator.

As shown in FIG. 19, the rotating plate 215 enables the operator to load the containers into the container staging area 214 outside of the container disassembly workspace 206. As the rotating plate 215 rotates, the containers 300 pass through an opening 808 in the shield assembly 800 and are positioned in the container disassembly workspace 206 with the container manipulation device 400 and the cutter device 402. In some embodiments, the rotating plate 215 is an oscillating or rotating plate that moves between the container staging area 214 and the container disassembly workspace 206.

The container manipulation device 400 includes the gripper 406 that is configured to grip and move one container 300 between at least a first position 408 proximate the container height scanner device 404 and a second position 410 proximate the cutter device 402 within the container disassembly workspace 206. The container height scanner device 404 is configured to sense the height of the container 300 to determine whether or not a container 300 is positioned in the first position 408 (e.g., to determine the presence of a container). The cutter device 402 includes a horn or cutter head 412 configured to cut through a wall of the container 300 to separate the first portion 312 of the container 300 from the second portion 314 of the container 300 when the container 300 is in the second position 410. The container barcode scanner device 405 scans the barcode on each container 300 to verify that the container has the correct barcode associated with the work order that generates the number of containers 300 needed to file the bulk container 302. More specifically, FIG. 20 illustrates four container barcode scanner devices 405 that each include a separate field of view 405a that captures a different portion of the container 300 as it passes from first position 408 to second position 410. In some embodiments, the four container barcode scanner devices 405 capture the entirety of the container 300 in the four fields of view 405A such that the barcode on the container 300 can be read no matter the orientation of the container 100.

During operation of the container disassembly workstation 125, the container manipulation device 400 is configured to grip the first portion 312 of the container 300 in a first, upright orientation 316 at the first position 408 such that a container longitudinal axis 311 is substantially aligned with the Z-direction and the lid 306 is vertically higher with respect to the Z-direction than the base 310. The container manipulation device 400 is also configured to move the container 300 from the first position 408 to the second position 410, and orient the container 300 in a second, upside-down orientation 318 at the second position. While in the second position 410, a second pair of grippers 407 hold the container 300 in the second orientation 318 and the cutter head 412 separates the first portion 312 from the second portion 314. The first portion 312 of the container 300 falls into a container chute 205 that extends through an opening 810 in a panel 804 of the shield assembly 800 and into a container receptacle 502.

The container manipulation device 400 is further configured to move the second portion 314 of the container 300 from the second position 410 to a third position 414, wherein the third position 414 is vertically above a pharmaceutical chute 207 that extends through an opening 812 in a panel 806 of the shield assembly 800. The container manipulation device 400 then orients the second portion 314 of the container 300 from the upside-down second orientation 318 to the upright orientation 316 to facilitate dumping the contents of the container onto the pharmaceutical chute 207. The container manipulation device 400 then deposits the empty second portion of the container 300 into a second container chute 209 that extends through an opening 814 in a panel 804 of the shield assembly 800 and into a second container receptacle 503.

A pharmaceutical receptacle assembly 204 is connected to base 200 and is configured to receive pharmaceuticals from the pharmaceutical chute 207. The pharmaceutical receptacle assembly 204 includes a pharmaceutical dust separation screen 232, a pharmaceutical dust receptacle 234, and a pharmaceutical receptacle 236. In this embodiment, the pharmaceutical receptacle 236 is positioned adjacent to the pharmaceutical dust receptacle 234 and the pharmaceutical dust separation screen 232 is positioned within a screen retention cavity of the pharmaceutical dust receptacle 234. In other embodiments, the pharmaceutical receptacle assembly 204 may be arranged in any manner that facilitates operation of the container disassembly workstation 125 as described herein.

In this embodiment, the pharmaceutical dust separation screen 232 is configured to retain the pharmaceuticals and to permit pharmaceutical dust to pass through the pharmaceutical dust separation screen 232 to enter the pharmaceutical dust receptacle 234. More specifically, pharmaceutical dust separation screen 232 includes holes 238 sized to facilitate pharmaceutical dust passing through the pharmaceutical dust separation screen 232 into a dust bucket 242 while facilitating retention of the pharmaceuticals against the pharmaceutical dust separation screen 232. In some embodiments, the pharmaceutical dust separation screen 232 is a stainless steel alloy. In some embodiments, the pharmaceutical dust separation screen 232 is any type of material and includes holes 238 that facilitate separation of pharmaceutical dust from the pharmaceuticals during operation of the container disassembly workstation 125.

In some embodiments, a vacuum system 240 is connected to the pharmaceutical dust receptacle 234 and is configured to apply a vacuum to the pharmaceutical dust receptacle 234 to facilitate drawing pharmaceutical dust through the pharmaceutical dust separation screen 232 and into the funnel-shaped pharmaceutical dust receptacle 234. In this embodiment, the pharmaceutical dust is stored in the dust bucket 242 proximate each container disassembly workstation 125. In some embodiments, the vacuum system 240 includes a centralized dust collection apparatus (not shown) coupled in flow communication with each of the workstations 125.

The pharmaceutical receptacle 236 includes a pharmaceutical receptacle funnel 246 configured to receive the pharmaceuticals from the pharmaceutical dust separation screen 232. As the dust separation screen 232 is rotated upwards, the pharmaceuticals are then directed by the pharmaceutical receptacle funnel 246 into one bulk container 302. In other embodiments, the pharmaceutical receptacle 236 includes any components in any configuration that facilitates the operation of container disassembly workstation 125 as described herein.

Figure 22:
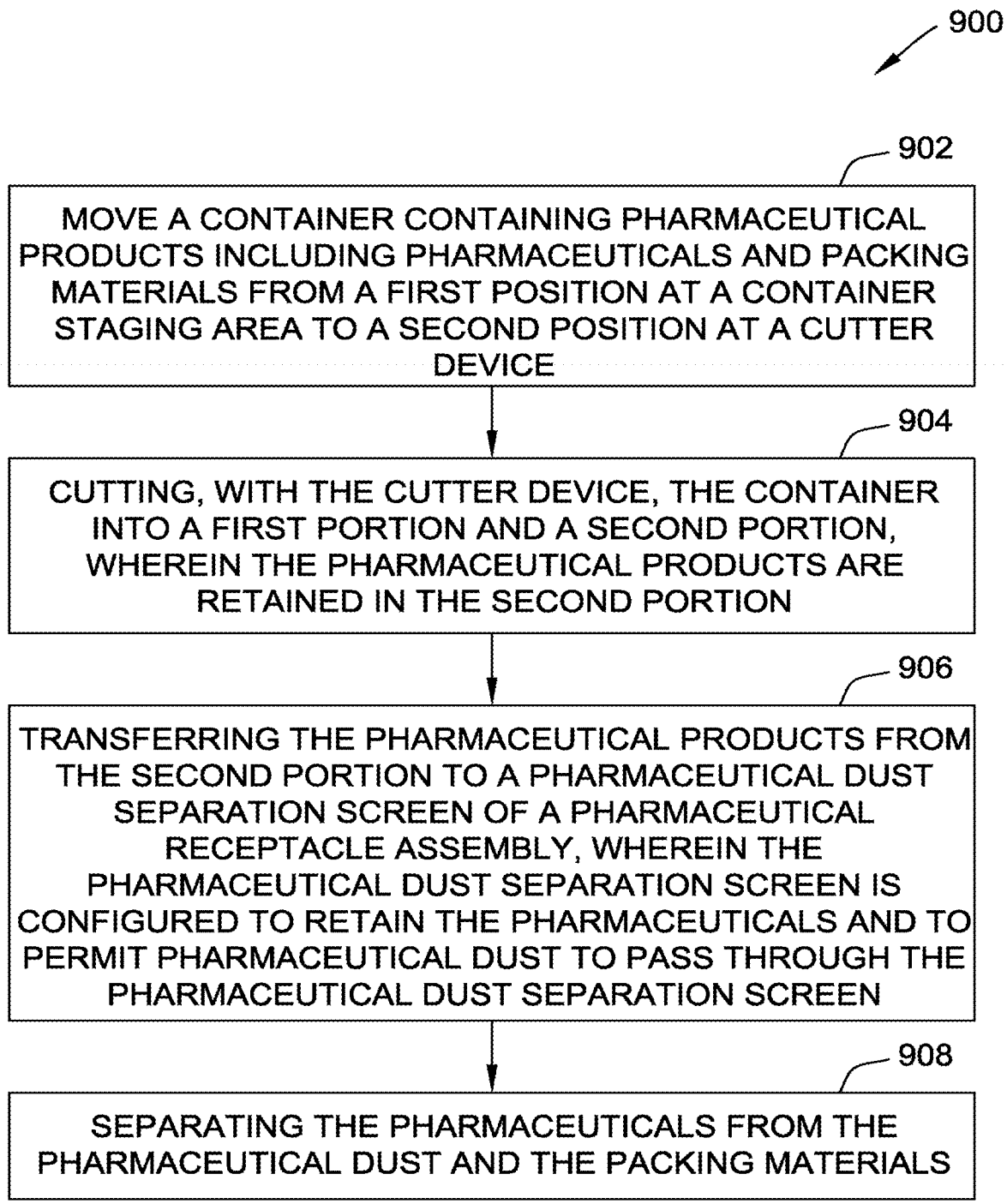
FIG. 22 is an example process flow illustrating a method for disassembly containers using a container disassembly workstation, according to an example embodiment.

FIG. 22 is an example process flow illustrating a method 900 for container disassembly according to an example embodiment. The method 900 may be performed on a container 300 that contains pharmaceuticals using a container disassembly workstation 125, or may otherwise be performed.

At block 902, the container 300 that contains pharmaceutical products including pharmaceuticals and packing materials is moved from the first position 408 at the container staging area 214 to the second position 410 at the cutter device 402.

At block 904, the cutter device 402 cuts the container 300 into the first portion 312 and the second portion 314 and the pharmaceutical products are retained in the second portion 314.

At block 906, the pharmaceutical products are transferred from the second portion 314 to a pharmaceutical dust separation screen 232 of a pharmaceutical receptacle assembly 204. In general, the pharmaceutical dust separation screen 232 is configured to retain the pharmaceuticals and to permit pharmaceutical dust to pass through the pharmaceutical dust separation screen 232.

The pharmaceuticals are separated from the pharmaceutical dust and the packing materials at block 706.

Embodiments of the methods and systems described herein achieve superior results as compared to prior methods and systems. For example, unlike some known pharmaceutical container disassembly systems, the pharmaceutical container disassembly and pharmaceutical bulk packaging systems described herein are configured to facilitate rapidly and efficiently transferring pharmaceuticals from relatively small volume containers to relatively larger volume containers while removing pharmaceutical dust, such as broken pills and desiccants. In particular, the container disassembly workstations described herein are operable such that pharmaceutical containers may be disassembled, and the pharmaceuticals contained therein removed, with reduced operator input required to separate the pharmaceuticals from packing materials and pharmaceutical dust as compared to known systems, enabling a greater throughput at each workstation and lessened residual pharmaceutical dust passed to downstream processes. As a result, pharmacies can be retrofitted with the container disassembly workstations, thereby increasing the efficiency and throughput of existing pharmacies. These workstations can have container manipulation devices that facilitate minimizing operator interaction with the container disassembly workstation during operation. Further, some workstations may have shielded workspaces to inhibit exposure of the operator to the workspace. Additionally, unlike some known pharmaceutical container disassembly systems, the workstations described herein are adjustable in height, can be of differing orientations, and can be constructed from modular components that do not require specialized tools or training to assemble.

The term "based on" or using, as used herein, reflects an open-ended term that can reflect others elements beyond those explicitly recited. Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for circuits or other electrical devices, which can be used in units, modules, systems, and sub-systems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

At least some portions of the present disclosure may be accomplished by using a robot. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

Methods and systems for pharmacy order processing, including removing pharmaceuticals from relatively small volume pharmaceutical containers and transferring the removed pharmaceuticals to relatively larger volume pharmaceutical containers using container disassembly workstations, especially in a high volume, specialty, or partially-automated order processing center are described herein. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The systems and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35

U.S.C. § 112(±) unless an element is expressly recited using the phrase "means for," or in the case of a method claim using the phrases "operation for" or "step for."

Embodiments for pharmacy order processing using container disassembly workstations are described above in detail. The systems and methods of operating such systems are not limited to the specific embodiments described herein, but rather, components of systems and/or steps of the methods may be utilized independently and separately from other components and/or steps described herein. For example, the methods may also be used in combination with other systems and environments and are not limited to the environments as described herein. Rather, the embodiments can be implemented and utilized in connection with many other applications.

In this specification and the claims, reference is made to a number of terms, which shall be defined to have the following meanings:

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

The term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, cd-roms, dvds, and any other digital source such as a network or the interne, as well as yet to be developed digital means, with the sole exception being a transitory, propagating signal.

The terms "software" and "firmware" are interchangeable, and include any computer program stored in memory for execution by devices that include, without limitation, mobile devices, clusters, personal computers, workstations, clients, and servers.

The term "computer" and related terms, e.g., "computing device", are not limited to integrated circuits referred to in the art as a computer, but broadly refers to a microcontroller, a microcomputer, a programmable logic controller (plc), an application specific integrated circuit, and other programmable circuits, and these terms are used interchangeably herein.

Computer systems are described, and such computer systems include a processor and a memory. However, any processor in a computer device referred to may also refer to one or more processors wherein the processor may be in one computing device or computing devices acting in parallel, such as in a cloud computing environment. Additionally, any memory in a computer device referred to may also refer to one or more memories, wherein the memories may be in one computing device or computing devices acting in parallel.

A processor may include any programmable system including systems using micro-controllers, reduced instruction set circuits (rise), application specific integrated circuits (asics), logic circuits, and any other circuit or processor capable of executing the functions described herein. The above examples are example only, and are thus not intended to limit in any way the definition and/or meaning of the term "processor." The term "database" may refer to either a body of data, a relational database management system (rdbms), or to both. A database may include any collection of data including hierarchical databases, relational databases, flat file databases, object-relational databases, object oriented databases, and any other structured collection of records or data that is stored in a computer system. The above are only examples, and thus are not intended to limit in any way the definition and/or meaning of the term database. Examples of rdbms's include, but are not limited to including, Oracle® Database, Mysql, IBM® Db2, Microsoft® Sql Server, Sybase®, and Postgresql. However, any database may be used that enables the systems and methods described herein. (oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In some embodiments, a computer program is embodied on a computer readable medium. In other embodiments, the system is executed on a single computer system, without requiring a connection to a server computer. In still other embodiments, the system is run in a windows® environment (windows is a registered trademark of Microsoft corporation, Redmond, Wash.). In yet another embodiment, the system is run on a mainframe environment and a Unix® server environment (Unix is a registered trademark of x/open company limited located in reading, Berkshire, United Kingdom). The application is flexible and designed to run in various different environments without compromising any major functionality. In some embodiments, the system includes multiple components distributed among computing devices. One or more components may be in the form of computer-executable instructions embodied in a computer-readable medium.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The inventive subject matter may be represented in a variety of different embodiments of which there are many possible permutations. Although specific features of various embodiments of the invention may be shown in some drawings and not in others, this is for convenience only. In accordance with the principles of the invention, any feature of a drawing may be referenced and/or claimed in combination with any feature of any other drawing. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A container disassembly workstation, comprising:
a base;
a desktop connected to the base, the desktop defining a container disassembly workspace; and
a receptacle assembly operably connected with the desktop, the receptacle assembly comprising:
a dust separation screen configured to retain objects and to permit dust to pass through the dust separation screen;
a dust receptacle configured to receive the dust separation screen and the dust from the objects;
an object receptacle including a receptacle funnel configured to receive the objects from the dust separation screen and a door connected to the receptacle funnel and configured to move between an open position and a closed position; and
a container support plate supported by the base, the desktop or a combination thereof, and extending at least partially into a container disassembly workspace, the container support plate being configured to receive a plurality of containers outside the container disassembly workspace and move the plurality of containers into the container disassembly workspace.

2. The container disassembly workstation of claim 1, wherein the container support plate includes a rotating support plate that is rotatable about an axis to move a set of the plurality of containers into the container disassembly workspace.

3. The container disassembly workstation of claim 2, wherein the rotating support plate including a plurality of receptacles to receive a container that holds a plurality of objects.

4. The container disassembly workstation of claim 3, wherein the rotating support plate is divided into at least two regions by an upright wall.

5. The container disassembly workstation of claim 4, wherein the desktop includes a shield assembly connected to the desktop to enclose the container disassembly workspace, and wherein the upright wall blocks an opening in the shield assembly through which the rotating support plate extends.

6. The container disassembly workstation of claim 5, further including:
a container manipulation device connected to the desktop and comprising a gripper, the container manipulation device configured to grip and move at least one container between at least a first position and a second position within the container disassembly workspace;
a scanner device connected to the desktop and configured to determine whether at least one container is positioned in the first position; and
a cutter device positioned adjacent the container manipulation device and comprising a cutter head and configured to cut through at least one wall of at least one container to separate at least a first portion of the at least one container from a second portion of the at least one container when the scanner device determines that at least one container is in the second position.

7. The container disassembly workstation of claim 6, wherein the container manipulation device is configured to:
grip a first portion of the at least one container in a first, upright orientation at the first position;
move the at least one container from the first position to the second position;
orient the at least one container in a second, upside-down orientation at the second position;
move the first portion of the at least one container from the second position to a third position, wherein the third position is vertically above the dust separation screen; and
orient the at least one container in the second, upside-down orientation.

8. The container disassembly workstation of claim 1, further including a shield assembly connected to the desktop to substantially surround the container disassembly workspace and configured to at least partially shield a technician from the container disassembly workspace, the shield assembly including an opening, and wherein the container support plate extends through the opening to allow containers to be loaded outside the container disassembly workspace and then moved though the opening by the container support plate into the container disassembly workspace.

9. The container disassembly workstation of claim 8, wherein the shield assembly further comprises an access door slidably or rotatably moveable between a closed position and an open position, wherein the open position facilitates access to the container disassembly workspace by an operator, and wherein the closed position inhibits access to the container disassembly workspace by the operator.

10. The container disassembly workstation of claim 9, further including a pair of operator gloves integral with the shield assembly enabling an operator to interact with the container disassembly workspace without direct exposure to the container disassembly workspace.

11. The container disassembly workstation of claim 8, wherein the shield assembly comprises a shield frame and a plurality of panels connected to the shield frame, wherein the opening is in one panel of the plurality of panels, and wherein the container disassembly workstation further comprises a pharmaceutical chute that extends through a chute opening in one panel of the plurality of panels.

12. The container disassembly workstation of claim 11, further including:
a container manipulation device connected to the desktop and comprising a gripper, the container manipulation device configured to grip and move at least one container between at least a first position and a second position within the container disassembly workspace;
a scanner device connected to the desktop and configured to determine whether at least one container is positioned in the first position; and
a cutter device positioned adjacent the container manipulation device and comprising a cutter head and configured to cut through at least one wall of at least one container to separate at least a first portion of the at least one container from a second portion of the at least one container when the scanner device determines that at least one container is in the second position.

13. The container disassembly workstation of claim 12, wherein the container manipulation device is configured to:
grip a first portion of the at least one container in a first, upright orientation at the first position;
move the at least one container from the first position to the second position;

orient the at least one container in a second, upside-down orientation at the second position;

move the first portion of the at least one container from the second position to a third position, wherein the third position is vertically above the dust separation screen; and orient the at least one container in the second, upside-down orientation.

14. The container disassembly workstation of claim 13, further comprising:

a vacuum system connected in flow communication with the dust receptacle, the vacuum system configured to apply a vacuum to the dust receptacle to draw dust through the dust separation screen and into the dust receptacle;

a bulk container receptacle configured to retain a bulk container proximate the object receptacle such that objects received by the object receptacle are directed into the bulk container; and wherein the object receptacle is positioned adjacent the dust receptacle and the dust separation screen is positioned within a screen retention cavity of the dust receptacle.

15. The container disassembly workstation of claim 1, wherein the dust separation screen includes a plurality of holes sized to facilitate pharmaceutical dust passing through the dust separation screen while facilitating retention of pharmaceuticals against the dust separation screen.

16. The container disassembly workstation of claim 1, wherein the container support plate includes an oscillating support plate that is movable about an axis to move a set of the plurality of containers into the container disassembly workspace.

17. The container disassembly workstation of claim 16, wherein the oscillating support plate including a plurality of receptacles to receive a container that holds a plurality of objects.

18. A method of disassembling a container comprising:

loading two or more containers onto a movable support plate;

moving the containers into a container disassembly workspace a container disassembly workstation;

opening, within the container disassembly workspace, a container including products and packing material to produce an opened container;

transferring, via a container manipulation device, the products from the opened container to a dust separation screen of a receptacle assembly, wherein the dust separation screen is configured to retain the products and to permit dust to pass through the dust separation screen;

separating the products from the dust and the packing material;

moving the products from a dust receptacle of the receptacle assembly to a bulk receptacle, wherein the bulk receptacle includes a receptacle funnel configured to receive the products from the dust separation screen and a door operably connected to the receptacle funnel and configured to move between an open position and a closed position; and disposing of the packing material.

19. The method of claim 18, wherein opening a container includes at least one of removing a lid of the container, separating a first portion of the container from a second portion of the container with a cutter device, and cutting through at least a portion of the container with the cutter device.

20. The method of claim 18, wherein loading includes loading a plurality of containers on a loadable portion of the movable support plate outside the container disassembly workspace with a disassembly portion of the movable support plate being positioned in the container disassembly workspace.

21. The method of claim 20, wherein moving the containers includes moving the loadable portion for the disassembly portion into the container disassembly workspace.

22. The method of claim 20, wherein opening the container comprises:

gripping the container in an upside down position, and cutting a bottom portion of the container with an automated cutter head including one of a blade or an ultrasonic device; and wherein transferring the pharmaceutical products comprises rotating the container into an upright orientation to empty the products on the dust separation screen.

* * * * *